United States Patent [19]

Colman et al.

[11] Patent Number: 5,663,294
[45] Date of Patent: Sep. 2, 1997

[54] CALPAIN-INHIBITING PEPTIDE ANALOGS OF THE KININOGEN HEAVY CHAIN

[75] Inventors: Robert W. Colman, Moylan, Pa.; Harlan N. Bradford, Lindenwold, N.J.; Bradford A. Jameson, Philadelphia, Pa.

[73] Assignee: Temple University of the Commonwealth System of Higher Education, Philadelphia, Pa.

[21] Appl. No.: 385,391

[22] Filed: Feb. 7, 1995

Related U.S. Application Data

[63] Continuation of Ser. No. 109,854, Aug. 20, 1993, abandoned, which is a continuation of Ser. No. 719,051, Jun. 21, 1991, abandoned.

[51] Int. Cl.⁶ .......................... A61K 38/00; A61K 38/02; C07K 5/00; C07K 7/00
[52] U.S. Cl. .......................... 530/326; 530/324; 530/327; 530/328; 530/329; 530/330; 530/325
[58] Field of Search .................................. 514/11, 12, 13, 514/14, 15, 16, 17; 530/324, 326, 327, 328, 317

[56] References Cited

FOREIGN PATENT DOCUMENTS 0 395 309 10/1991 European Pat. Off. .

OTHER PUBLICATIONS

Ishiguru et al., *Biochemistry*, vol. 26, No. 28, (1987), pp. 7027–2028.
Bradford et al., *Biochemical Journal*, vol. 270, No. 1 (1990) pp. 88–89.
Higashiyama et al., *Biochemistry*, vol. 25, pp. 1669–1675 1986.
Matsueda et al., Chemistry Letters, No. 2, pp. 191–194, Feb. 1990.
Puri et al., Transactions of the Assoc. of Am. Phys., vol. CII, pp. 13–19, 1989.
Salnesen et al., Biochem J., vol. 234, pp. 429–434, 1986.
Salvesen et al., *Biochem J.* 234, 429–434 (1986).
Muller–Esterl, *Atemw. Lungenkrkh. Jahrgang* 14, 1. Suppl. Heft S11–S22 (1988).
Teno et al., *Int. J. Peptide Protein Res.* 30, 93–98 (1987).
Matsueda et al., *Chem. Lett.* 191–194 (Feb. 1990).
Puri et al., *Trans. Assoc. Amer. Physicians* 102, 13–19 (1990).

*Primary Examiner*—Avis M. Davenport
*Attorney, Agent, or Firm*—Seidel, Gonda, Lavorgna & Monaco, PC

[57] ABSTRACT

Synthetic peptide analogs of human kininogen are provided which are conformationally restricted by means of intramolecular bonding. The peptides mimic the biological activity of human kininogen by inhibiting the activity of the biologically significant protease, calpain. The peptides are designed by means of an equilibrium conformational model of the kininogen heavy chain.

33 Claims, 1 Drawing Sheet

CALPAIN-INHIBITING PEPTIDE ANALOGS OF THE KININOGEN HEAVY CHAIN

This is a continuation of application Ser. No. 08/109,854 filed on Aug. 20, 1993 now abandoned, which is a continuation of application Ser. No. 07/719,051 filed on Jun. 21, 1991, now abandoned.

REFERENCE TO GOVERNMENT GRANT

The invention described herein was supported in part by National Institutes of Health grant HL 24365.

FIELD OF THE INVENTION

The invention relates to synthetic peptide analogs of the human plasma proteins, high and low molecular weight kininogen.

BACKROUND OF THE INVENTION

Activation and aggregation of human platelets leads to the formation of blood clots (thrombi). It is well established that the binding of fibrinogen to specific receptors on platelets is essential for platelet aggregation. Unstimulated platelets do not bind fibrinogen and do not aggregate during circulation. When platelets are stimulated by certain physiological agonists, such as ADP, thrombin, etc., the fibrinogen receptors associated with the glycoprotein IIb/IIIa complex on the platelet become exposed, resulting in fibrinogen binding leading to platelet aggregation.

Aggregin ($M_r$=100 kDa) is a putative ADP-receptor on the platelet surface. It has been shown to be completely cleaved during thrombin- and plasmin-induced platelet aggregation. The binding of thrombin and plasmin to their receptors on the platelet surface is a important requirement for these plasma proteases to elicit aggregin proteolysis and platelet aggregation.

Thrombin- and plasmin-induced platelet aggregation and cleavage of aggregin are indirectly mediated by intracellularly activated calpain expressed on the platelet surface. Thrombin- and plasmin-induced platelet aggregation are inhibited by cysteine protease inhibitors, including kininogens.

Kininogens exist in human plasma in two molecular forms, high molecular weight kininogen (HK) and low molecular weight kininogen (LK). HK is synthesized in the liver as a single chain and secreted into plasma at a concentration of 0.67 µM. HK is cleaved by plasma kallikrein, resulting in the formatign of (i) a 64 kDa heavy chain and a 56 kDa light chain linked.by a single disulfide bond, and (ii) the nonapeptide bradykinin. The latter has multiple inflammatory effects including induction of pain, vasodilation and increased vascular permeability (Colman, J. Clin. Invest. 73, 1249–1253 (1984)). Studies of human mutants (e.g., Colman et al., J. Clin. Invest. 56, 1650–1662 (1975)) delineated the coagulant function of HK. LK, present in plasma at 2.4 µM, releases bradykinin preferentially after exposure to tissue kallikrein, and does not exhibit coagulant activity. LK contains a short light chain of 4 kDa, and has a total molecular weight of 66 kDa, in contrast to the 56 kDa light chain and 120 kDa total weight of intact HK. Both HK and LK have an identical heavy chain which results from translation of alternately spliced mRNAs from a single gene.

The major function of the heavy chain of HK and LK is to inhibit proteases with cysteine at their active sites. Such cysteine proteases include the calcium-activated cysteine proteases, more commonly known as "calpains" (Schmaier et al., J. Clin. Invest. 77, 1565–1573 (1986)). The kininogen heavy chain contains three repeating units or "domains" having mutual sequence homology, designated D1, D2, and D3. The domains are derived evolutionarily from the more primitive stefins and cystatins by gene duplication. The crystal structure of chicken egg white cystatin has been solved by Bode et al., EMBO J., 7, 2593–2599 (1988).

Of the three kininogen heavy chain repeats, D2 and D3 contain the pentapeptide Gln-Val-Val-Ala-Gly ("QWAG"). Although both D2 and D3 contain the QVVAG sequence and are inhibitors of cysteine proteinases, only D2 is effective in inhibiting calpain (Salvesen et al., Biochem. J. 234, 429–434 (1986); Muller-Esterl, Atemw.-Lunqenkrkh. Jahrganq 14, 1.Suppl.-Heft S11–S22 (1988). Teno et al., Int. J. Peptide Protein Res. 30, 93–98 (1987) report weak activity of the QVVAG pentapeptide in inhibiting the thiol protease papain.

Reocclusion of coronary arteries is a frequent complication following thromboiytic therapy. It has been postulated that reocclusion is due to plasmin-induced activation of platelets. High concentrations of plasmin, such as might occur in therapeutic thrombolysis, are known to cause platelet aggregation.

Coronary artery restenosis following angioplasty has been linked to platelet activation by protease agonists. Restenosis may be initiated by thrombin-stimulated release of growth factors from platelets.

What is needed is a method of inhibiting stimulation and aggregation of platelets by protease agonists, specifically a method of inhibiting stimulation of platelets by inhibiting the action of platelet calpain in facilitating thrombin- and plasmin-induced platelet aggregation.

SUMMARY OF THE INVENTION

A synthetic peptide is provided comprising an amino acid sequence corresponding to a portion of domain 2 of the human kininogen heavy chain. The peptide has a restricted conformation and the ability to inhibit the enzymatic activity of calpain.

In another embodiment, the invention is directed to a method of designing a peptide analog to the kininogen heavy chain domain. The distance between two parts of a molecular model of the kininogen heavy chain domain 2 is determined at confirmational equilibrium. The primary structure of the domain is then modified to restrict that distance to the determined distance. A peptide comprising the modified primary structure is then synthesized.

In yet another embodiment of the invention, a method of producing a peptide having a restricted confirmation is provided. Accordingly, a peptide having an amino acid sequence corresponding to a portion of the human kininogen heavy chain domain 2 is provided. The confirmational equilibrium of a portion of that domain is determined. A covalent modification is introduced into the peptide to restrict a distance between two parts of the peptide to a distance between corresponding parts of the peptide in the equilibrium confirmation determined.

The invention further provides pharmaceutical compositions comprising one or more of the peptides in combination with a pharmaceutically acceptable carrier. The activity of platelet calpain is inhibited by the peptides of the invention. Inhibition of platelet calpain results in the inhibition of thrombin- or plasmin-induced platelet aggregation of human platelets incubated with calpain-inhibiting agents.

By "human kininogen heavy chain" is meant the about 64 kDa polypeptide chain, common to both high molecular weight and low molecular weight human kininogen, which polypeptide is obtainable by kallikrein cleavage of high about 120 kDa major kallikrein cleavage fragment and isolation of the about 64 kDa single polypeptide chain therefrom.

By "domain 2" of human kininogen heavy chain is meant the region of the intact 64 kDa polypeptide chain comprising from about amino acid 124 to about amino acid 243 of the mature polypeptide. The mature polypeptide is generated by a post-translational modification which cleaves an 18-amino acid leader from the translated polypeptide.

DESCRIPTION OF THE FIGURES

FIG. 1 is a plot of calpain inhibition by the following peptide, (SEQ ID NO:1)
Cys Thr Asp Asn Ala Tyr Ile Asp Ile Gln
                5                      10
Leu Arg Ile Ala Ser Phe Ser Gln Asn Cys
            15                    20 which peptide corresponds to human kininogen heavy chain amino acids 229 through 248 (corresponding to amino acids 211–230 of the mature polypeptide), with an intramolecular disulfide bond connecting the cysteine residues.

DETAILED DESCRIPTION OF THE INVENTION

Figure 1:
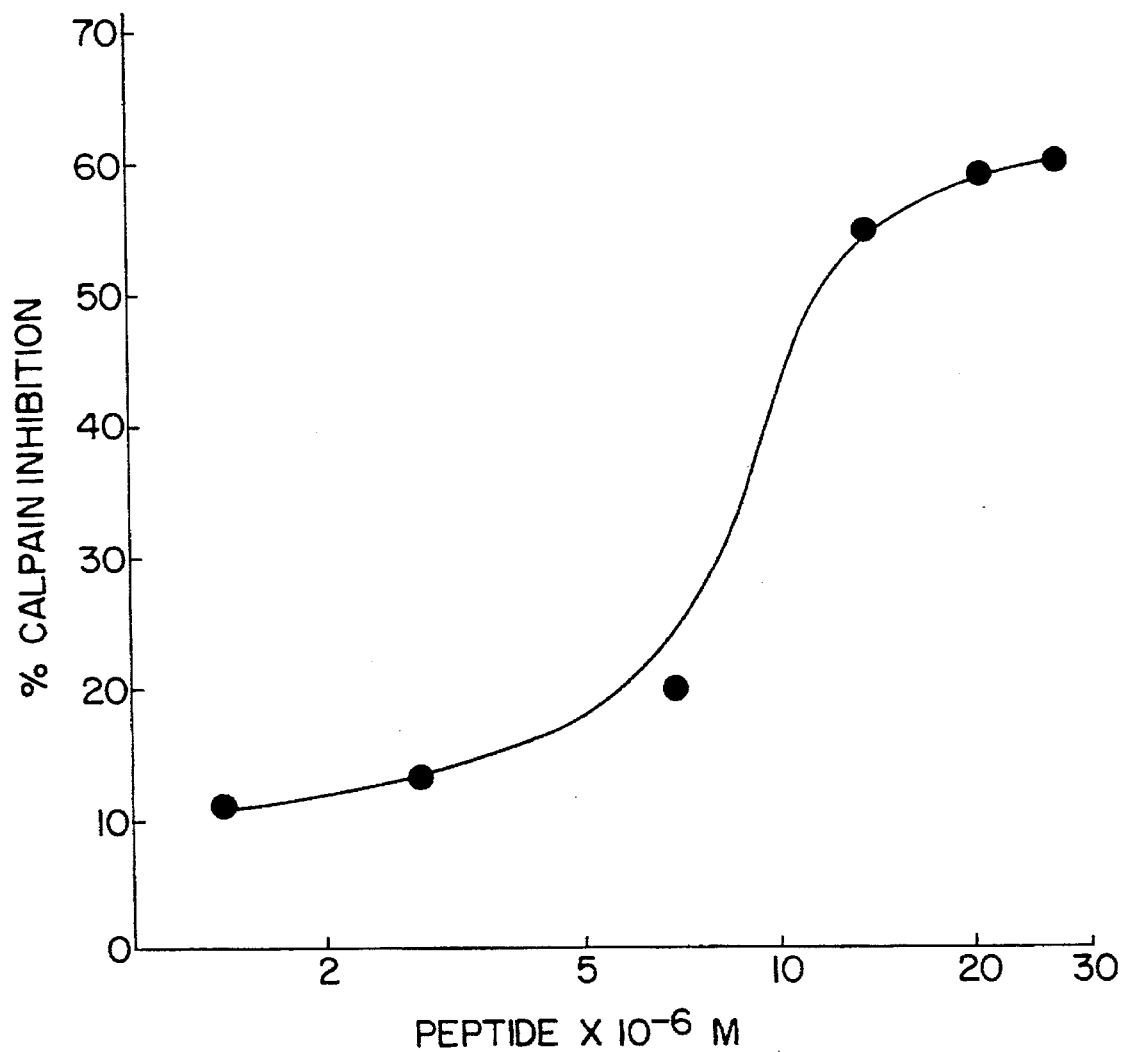

We have found that there is a specific site in the kininogen heavy chain, in addition to the QVVAG sequence, which is a binding or inhibitory site involved in calpain inhibition. The site lies within domain 2. The deduction of the structure of domain 2 was accomplished a homology-based molecular modeling technique reviewed by Jameson in *Nature*, 341, 465–466 (1989), based upon the published structure of cystatin (Bode et al., *Embo J.* 7, 2593–2599 (1988)). Cystatin, like kininogen, is a cysteine protease inhibitor. The modeled domain 2 structure is used as a design template for synthesizing peptides according to the present invention that are expected to adopt a conformational repertoire overlapping that of the native protein. The sequences identified herein from the kininogen heavy chain have not been previously identified as being inhibitory for cysteine proteases.

The calpain-inhibiting peptides of the invention are believed capable of selectively inhibiting platelet activation by thrombin and/or plasmin. Other peptides, such as the RGD-containing proteases, may inhibit platelet aggregation in response to cell agonists, but may also lead to prolonged bleeding times and hemorrhagic complications.

The primary structure of the kininogen heavy chain is known (Salveson et al., *Biochem. J.* 234, 429–434 (1986), incorporated herein by reference; Kellerman et al., *J. Biochem.* 154, 471–478 (1986)) incorporated herein by reference). While the significance of the QVVAG sequence as a weak inhibitor of papain is known (Tenno et al., *Int. J. Peptide Protein Res.* 30, 93–98 (1987)), the prior art attaches no functional significance to any other sequence as a potential inhibitor of calpain.

Traditional syntheses of the linear amino acid sequence of biologically interesting proteins may result in peptides that are either biologically inactive or, at best, marginally active. We have created a molecular model of the three-dimensional structure of heavy chain domain 2. The structure created in this manner is used as a template for designing conformationally-restricted synthetic analogs having calpain inhibiting activity. Using both distance and geometric constraints imparted through measurements of the subdomains within the calculated structure, constraints are artificially introduced, e.g., disulfide bonds, to limit the conformational freedom of a synthetic peptide that incorporates the relevant amino acids. One particular conformationally-restricted synthetic peptide analog having potent calpain inhibiting activity corresponds to kininogen heavy chain residues 211–230, according to the numbering of the amino acids of the mature polypeptide. The model disclosed herein may be utilized to prepare additional conformationally-restricted synthetic peptides having similar activity.

Appendix 1 hereto contains the set of Brookhaven coordinates and connect statement specifying our equilibrium conformation model of the major portion of kininogen heavy chain domain 2 comprising the 109 amino acids spanning positions 124 to 232, inclusive. The corresponding graphic molecular model satisfying these coordinates may be generated by inputting the coordinates and connect statement into any of the many commercially available molecular modeling programs which are capable of reading files in the Brookhaven format. Such programs include, for example, those of BioDesign, Inc., Pasadena, Calif.; Biosym Technologies, San Diego, Calif.; Tripos, St. Louis, Mo.; Polygen, Waltham, Mass.; and Chemical Design Ltd., Oxford, UK. The data may be entered as an ASCII file.

According to the Brookhaven format shown in the Appendix, each of the atoms of kininogen heavy chain residues 124–232 is assigned a number and respective X, Y and Z coordinates. The coordinate portion of the listing begins with the cysteine residue (CYS 1) at position 124 of the mature kininogen heavy chain. The atom types are identified as "N" for nitrogen, "HN" for hydrogen which is connected to a nitrogen atom, "C" for carbon, "CA" for $\alpha$ carbon, "CB" for $\beta$ carbon, "CG" for $\gamma$ carbon, and so forth. Identical atoms of branched side chains are indicated by numbers. Thus, the two $\gamma$ carbons of VAL 5 are designated "CG 1" and "CG 2" respectively.

The data file further comprises a connect statement which begins immediately after the coordinates for atom 1068. The connect statement identifies the covalent bonding pattern of each of the 1068 atoms. Thus, for example; the 10th entry of the connect statement (CONNECT 10) indicates that atom 10, which is the nitrogen atom of LEU 2 (corresponding to amino acid 125 of the mature kininogen heavy chain sequence), is bonded to atom 12 (the $\alpha$ carbon of the same residue), atom 6 (the carbonyl carbon of the neighboring cysteine residue), and atom 11 (hydrogen). The complete data file of 1,068 coordinates, together with the connect statement for these entries, specifies the equilibrium conformation of kininogen heavy chain domain 2.

The analogs of the invention generally have an amino acid sequence similar to the native domain 2 sequence. However, a covalent modification is introduced to restrict the analog to the conformation (or one close to it) displayed by the above model. Generally, this is accomplished by determining a distance between two non-contiguous parts of the amino acid chain according to the model. Then a chemical moiety is introduced to fix that determined distance in the analog. For example, a 5-6A distance can be fixed using a disulfide bond. Cysteine residues can be introduced at the appropriate positions in the model and then the new cysteine-containing model is tested for its ability to mimic the structure observed in the model.

The use of artificially introduced cysteine residues to create a disulfide bridge is one way to conformationally restrict the peptides. Disulfide bonds, however, are intrinsically unstable and it is difficult to obtain a homogeneous solution of intradisulfide-bonded species without concomitant mixed disulfides. The disulfide bridges can be replaced in biologically active peptides by stable covalent bonds. There are several strategies which can be utilized in the covalent closure of the peptides. Two of these strategies are described below.

The peptide can be internally crosslinked via the side chains of a lysine ε-amino group and the carboxylic acid function of a glutamic or aspartic acid side chain, thus creating an amide bond. The peptide is synthesized according to standard procedures on a low substitution (0.2 mM/gm or less) para-methylbenzhydrylamine resin. The first residue added to the resin is an N-α-tBOC,ε-fMOC lysine. The rest of the peptide synthesis is continued normally using tBOC chemistry until the final residue is added. The last residue to be added is a Z-protected glutamic acid, where the carboxylic acid moiety is protected with a tert-butyl group. Treatment of the peptide resin with piperidine/DMF removes the fMOC group from the ε-amino group of the initial lysine without affecting any other protection groups. Subsequent treatment with trifluoracetic acid removes the protection of the carboxylic acid group of the glutamic acid. Following neutralization, the peptide is covalently closed using a standard diimide-meditated coupling reaction. It should be emphasized that this is only one of the ways in which the synthetic peptide can be covalently closed.

Other fMOC/tBOC strategies include covalent closure of the peptide between two free amino groups utilizing toluene-2,4-diisocyanate (TDI), a heterobifunctional cross-linker. The methyl group of the aromatic ring of TDI prevents the isocyanate group in the 2 position from reacting at a pH 7.5 or below, whereas the isocyanate group in the para position is highly reactive. A shift in pH to greater than 9.0 will initiate a reaction with the isocyanate group in the 2 position, thus enabling highly specific and controlled conditions for covalent closure of the peptide. By utilizing a variety of different strategies for restricting the conformation of these peptides, distance geometries and orientation of the folded peptide can be controlled. Any such strategies employing chemical reactions known in the art may be used.

Using these techniques, synthetic peptide analogs can be made and tested for their ability to mimic the biological functions of the parent kininogen molecule, specificially, calpain inhibition.

One particularly useful peptide analog which was derived using the techniques described herein comprises amino acids 211–230 of the kininogen heavy chain. This peptide was restricted conformationally using cysteine-cysteine disulfide bonds, but other restricting means may be advantageously used. Peptide 211–230, crosslinked at cysteine residues 211 and 230, inhibits the activity of calpain, and, as a consequence, may be used to inhibit platelet activation by thrombin and/or plasmin. Methods of assaying calpain inhibition are known in the art. One such method is described hereinafter in Example 2. Another method is described in Example 19 of European Patent Application 393,457 (1990).

The present peptides are relatively short in length and therefore they are easily synthesized by chemical means. Such synthetic peptides have many advantages over the use of the entire kininogen heavy chain, or the entire D2 domain. Large portions of the heavy chain cannot conveniently be made by synthetic techniques and must be made by recombinant DNA techniques, which are expensive and time consuming. Additionally, proteins may present solubility and immunogenicity problems when introduced into a patient. Short synthetic peptides are much more soluble and less immunogenic than larger proteins.

As used herein, "peptide" refers to a linear series of no more than about 50 amino acid residues connected to one another by peptide bonds between the alpha-amino groups and carboxy groups of adjacent amino acid residues. Additional covalent bonds between portions of the peptide are also present to restrain the conformation of the molecule, such as amide and disulfide bonds. When used herein, "protein" refers to a linear series of greater than 50 amino acid residues connected one to the other as in a peptide. The term "synthetic peptide" means a chemically derived chain of amino acid residues linked together by peptide bonds that is free of naturally occurring proteins and fragments thereof.

The three-letter symbols used to represent the amino acid residues in the peptides of the present invention are those symbols commonly used in the art. The amino acid residues are preferred to be in the "L" isomeric form. However, residues in the "D" isomeric form may be substituted for any L-amino acid, as long as the desired functional property of calpain inhibition is retained by the peptide. The three-letter symbols used herein refer to the following amino acids: Ser is serine; Ile is isoleucine; Gln is glutamine; Phe is phenylalanine; His is histidine; Trp is tryptophan; Lys is lysine; Asn is asparagine; Leu is leucine; Gly is glycine; Thr is threonine; Asp is aspartic acid; Arg is arginine; and Ala is alanine.

Peptides of the present invention include any analog, fragment or chemical derivative of the peptides capable of inhibiting calpain. The term "analog" refers to any peptide having a substantially identical amino acid sequence to the peptides of the invention in which one or more amino acids have been substituted with other amino acids; the substituted amino acids allow or require the peptide to assume the equilibrium conformation of the domain of the parent protein. Often, cysteine, lysine and glutamic acid will be used for their side chains which can form covalent linkages to restrict the conformation of a peptide. In addition, conservative amino acid changes may be made which do not alter the biological function of the peptide. For instance, one polar amino acid, such as glycine, may be substituted for another polar amino acid; or one acidic amino acid, such as aspartic acid may be substituted for another acidic amino acid, such as glutamic acid; or a basic amino acid, such as lysine, arginine or histidine may be substituted for another basic amino acid; or a non-polar amino acid, such as alanine, leucine or isoleucine may be substituted for another non-polar amino acid.

The term "analog" shall also include any peptide which has one or more amino acids deleted from or added to an amino acid sequence of kininogen heavy chain domain 2, but which still retains a substantial amino acid sequence homology to kininogen, as well as kininogen's calpain inhibiting activity. A substantial sequence homology is any homology greater than 50% but preferably greater than 90%. The term "fragment" shall refer to any shorter version of the peptides identified herein having at least five amino acid residues, wherein the fragment is capable of inhibiting calpain.

The peptides of the present invention may be prepared by any of the following known techniques. Conveniently, the peptides may be prepared using the solid-phase synthetic technique initially described by Merrifield, in *J. Am. Chem. Soc.* 15, 2149–2154 (1963). Other peptide synthesis techniques may be found, for example, in M. Bodanszky et al., *Peptide Synthesis*, John Wiley & Sons, 2d Ed. (1976) as well as in other reference works known to those skilled in the art. A summary of peptide synthesis techniques may be found in J. Stuart and J. D. Young, *Solid Phase Peptide Synthelia*, Pierce Chemical Company, Rockford, Ill. (1984). The synthesis of peptides by solution methods may also be used, as described in *The Proteins*, vol- II, 3d Ed., Neurath, H. et al., Eds., p. 105–237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973). Of course, the present peptides may also be prepared by recombinant DNA techniques, although such methods are not preferred because of the need for purification and subsequent chemical modifications to conformationally restrain the peptides.

In general, these synthetic methods involve the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group, such as lysine.

Using a solid phase synthesis as an example, the protected or derivatized amino acid is attachedto an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are devoid of benzylated or methylbenzylated amino acids. Such protecting group moieties may be used in the course of synthesis, but they are removed before the peptides are used. Additional reactions may be necessary, as described elsewhere to form intramolecular linkages to restrain conformation.

The peptides of the present invention generally contain at least five amino acid residues and up to fifty amino acid residues, preferably between 6 and 20 amino acid residues. These peptides may be linked to an additional sequence of amino acids either or both at the N-terminus and at the C-terminus, wherein the additional sequences are from 1–100 amino acids in length. Such additional amino acid sequences, or linker sequences, can be conveniently affixed to a detectable label or solid matrix, or carrier. Typical amino acid residues used for linking are tyrosine, cysteine, lysine, glutamic acid and aspattic acid, or the like.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such a mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

For use in a method of treatment, such as treatment for inhibiting thrombin- or plasmin-induced platelet aggregation, the synthetic peptides of the present invention may be present in a pharmaceutical composition in admixture with a pharmaceutically-acceptable carrier. The pharmaceutical composition may be compounded according to conventional pharmaceutical formulation techniques. The Carrier may take a wide variety of forms depending on the form of preparation desired for administration, e.g., sublingual, rectal, nasal, oral or parenteral. Compositions for oral dosage form may include any of the usual pharmaceutical media, such as, for example, water, oils, alcohols, flavoring agents, preservatives, coloring agents and the like in the case of oral liquid preparations (e.g., suspensions, elixirs and solutions) or carriers such as starches, sugars, diluents, granulating agents, lubricants, binders, disintegrating agents and the like in the case of oral solid preparations (e.g., powders, capsules and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For compositions to be administered parenterally, the carrier will usually comprise sterile water, although other ingredients to aid solubility or for preservation purposes may be included. Injectable suspensions may also be prepared, in which case appropriate liquid carriers, suspending agents and the like may be employed. The parenteral routes of administration may be intravenous injection, intramuscular injection or subcutaneous injection.

For intravenous administration, the peptides may be dissolved in an appropriate intravenous delivery vehicle containing physiologically compatible substances such as sodium chloride, glycine and the like, having a buffered pH compatible with physiologic conditions. Such intravenous delivery vehicles are known to those skilled in the art.

The peptides of the invention may be administered to subjects in any situation where inhibition of calpain activity is desired. Calpain inhibitors may be administered during or after angioplasty or thrombolytic therapy to prevent restenosis or reocclusion. It is believed that restenosis following angioplasty may be initiated by thrombin-stimulated release of growth factors from platelets. Reocclusion, a frequent occurrence after thrombolytic therapy, has been postulated to be caused by plasmin-induced activation of platelets, which is mediated by platelet calpain.

The peptides may be administered by any convenient means which will result in the delivery to the bloodstream of a calpain-inhibiting effective amount. Intravenous administration is presently contemplated as the preferred administration route. The amount administered will depend on the activity of the particular compound administered, which may readily be determined by those of ordinary skill in the art. Generally, the peptides may be administered in an amount sufficient to provide a plasma concentration in the range of from about 10 to about 500 μM, more preferably in the range of from about 50 to about 250 μM. Plasma concentrations higher or lower than these may be utilized, depending upon the activity of the particular compound being administered, and the nature of the treatment.

In addition to inhibition of plasmin- and thrombin-induced platelet aggregation, inhibitors of calpain have other beneficial therapeutic utilities. Abnormal activation of calpain has been linked to diverse disease conditions, such as muscular dystrophy and cataracts. Furthermore, inhibitors of calpain have been shown to be able to limit brain damage caused by the interruption of the supply of blood and oxygen to the brain. Tests with calpain inhibitors in model systems have indicated that inhibition of calpain alone is sufficient to protect brain cells from ischemic damage after ischemic attack. It is contemplated that the peptides of the present invention are useful in any therapeutic circumstance where reduction of calpain activity is desired.

The following non-limiting examples serve to illustrate the practice of the invention.

EXAMPLE 1

This example demonstrates the selection and synthesis of a calpain-inhibiting kininogen analog.

The modeled structure of Appendix 1 was used as a design template in the construction of an analog corresponding to kininogen heavy chain residues 211–230. In order to conformationally restrict the folding equilibria of the resulting synthetic peptide, the cysteine residues at positions 211 and 230 were allowed to form an intrachain disulfide bond in computer-assisted modeling. The predicted folding pattern of the putative structure was tested for its ability to mimic the structure observed in our model of domain 2. Finding satisfactory agreement, the peptide was synthesized according to conventional solid phase procedures. The peptide incorporated the native residues 211–230, with a disulfide residue bond connecting the cysteine residues at positions 211 and 230. The peptide assayed pure upon high performance liquid chromatography. The intrachain disulfide bond was spontaneously formed by diluting the synthesized peptide to a concentration of 100 μg/ml in a solution adjusted to pH 8.5 with $NH_4OH$, followed by stirring open to the atmosphere to ensure oxidation. The resulting disulfide-bonded peptide was then lyophilized.

EXAMPLE 2

This example demonstrates the biological activities of the peptide analogs.

The calpain-inhibiting activity of the disulfide-bonded Example 1 peptide was demonstrated according to a modification of the procedure of Schmaier et al., *J. Clin. Invest.* 77, 1565 (1986). A calpain preparation (5–10 μl) was placed on a floating filter membrane (Marusyk et al., *Anal. Biochem.* 105, 403 (1980)) (Millipore type VMWP) over a buffer containing 50 mM Tris/HCl, pH 7.5 and 2.5 mM EDTA for 45–60 minutes, then carefully removed and used for the following inhibition study. Aliquots (25 μl) of the enzyme (calpain) and buffer or synthetic peptide were added to a cuvette at 25° C. containing 1 mM succinyl-Leu-Tyr-amino-4-methylcumarin as the substrate in a buffer consisting of 60 mM Tris/HCl, pH 7.5, 2.5% DMSO and 5 mM $CaCl_2$. The rate of substrate hydrolysis was continuously recorded on a Perkin-Elmer LS-5 fluorescence spectrophotometer connected to a R100 chart recorder. The absorbance maximum of substrate occurred at 380 nm and emission maximum was observed at 450 nm. The data, forming a dose-dependent curve, was plotted in FIG. 1. The $IC_{50}$ calculated from FIG. 1 corresponds to that concentration of inhibitory peptide that produced 50% inhibition of calpain activity. The subject peptide inhibited calpain activity with an $IC_{50}$ of 26 μM.

All references with respect to synthetic, preparative and analytic procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

APPENDIX 1

Kininogen Heavy Chain Domain 2

| | | | | | | | |
|---|---|---|---|---|---|---|---|
| ATOM | 1 | N | CYS | 1 | 148.052 | 83.819 | 84.352 |
| ATOM | 2 | HN | CYS | 1 | 149.065 | 83.809 | 84.469 |
| ATOM | 3 | HN | CYS | 1 | 147.668 | 82.917 | 84.631 |
| ATOM | 4 | HN | CYS | 1 | 147.824 | 83.997 | 83.373 |
| ATOM | 5 | CA | CYS | 1 | 147.470 | 84.875 | 85.190 |
| ATOM | 6 | C | CYS | 1 | 147.825 | 86.268 | 84.842 |
| ATOM | 7 | O | CYS | 1 | 146.840 | 86.969 | 84.504 |
| ATOM | 8 | CB | CYS | 1 | 147.644 | 84.558 | 86.684 |
| ATOM | 9 | SG | CYS | 1 | 146.110 | 84.227 | 87.512 |
| ATOM | 10 | N | LEU | 2 | 149.077 | 86.741 | 84.892 |
| ATOM | 11 | HN | LEU | 2 | 149.734 | 86.089 | 85.056 |
| ATOM | 12 | CA | LEU | 2 | 149.566 | 88.045 | 84.751 |
| ATOM | 13 | C | LEU | 2 | 148.668 | 89.216 | 84.556 |
| ATOM | 14 | O | LEU | 2 | 148.323 | 89.566 | 83.403 |
| ATOM | 15 | CB | LEU | 2 | 150.948 | 88.103 | 84.078 |
| ATOM | 16 | CG | LEU | 2 | 151.989 | 88.607 | 85.088 |
| ATOM | 17 | CD1 | LEU | 2 | 152.870 | 87.455 | 85.583 |
| ATOM | 18 | CD2 | LEU | 2 | 152.865 | 89.687 | 84.451 |
| ATOM | 19 | N | GLY | 3 | 148.176 | 89.956 | 85.546 |
| ATOM | 20 | HN | GLY | 3 | 147.620 | 90.678 | 85.315 |
| ATOM | 21 | CA | GLY | 3 | 148.425 | 89.744 | 86.899 |
| ATOM | 22 | C | GLY | 3 | 147.373 | 90.110 | 87.855 |
| ATOM | 23 | O | GLY | 3 | 147.594 | 91.136 | 88.542 |
| ATOM | 24 | N | CYS | 4 | 146.233 | 89.466 | 88.067 |
| ATOM | 25 | HN | CYS | 4 | 145.730 | 89.717 | 88.819 |
| ATOM | 26 | CA | CYS | 4 | 145.657 | 88.447 | 87.302 |
| ATOM | 27 | C | CYS | 4 | 144.407 | 88.893 | 86.629 |
| ATOM | 28 | O | CYS | 4 | 144.267 | 88.580 | 85.428 |
| ATOM | 29 | CB | CYS | 4 | 145.512 | 87.173 | 88.159 |
| ATOM | 30 | SG | CYS | 4 | 144.869 | 85.790 | 87.252 |
| ATOM | 31 | N | VAL | 5 | 143.398 | 89.595 | 87.136 |
| ATOM | 32 | CA | VAL | 5 | 143.310 | 90.159 | 88.410 |
| ATOM | 33 | C | VAL | 5 | 142.944 | 89.243 | 89.505 |
| ATOM | 34 | O | VAL | 5 | 143.802 | 89.121 | 90.419 |
| ATOM | 35 | CB | VAL | 5 | 142.824 | 91.626 | 88.411 |
| ATOM | 36 | CG1 | VAL | 5 | 141.331 | 91.877 | 88.673 |
| ATOM | 37 | CG2 | VAL | 5 | 143.681 | 92.475 | 89.357 |
| ATOM | 38 | N | HIS | 6 | 141.780 | 88.605 | 89.495 |
| ATOM | 39 | HN | HIS | 6 | 141.248 | 88.691 | 88.725 |
| ATOM | 40 | CA | HIS | 6 | 141.277 | 87.824 | 90.533 |
| ATOM | 41 | C | HIS | 6 | 141.564 | 86.374 | 90.452 |
| ATOM | 42 | O | HIS | 6 | 142.278 | 86.055 | 91.436 |
| ATOM | 43 | CB | HIS | 6 | 139.820 | 88.188 | 90.854 |
| ATOM | 44 | CG | HIS | 6 | 139.748 | 89.140 | 91.966 |
| ATOM | 45 | ND1 | HIS | 6 | 139.722 | 90.444 | 91.890 |
| ATOM | 46 | HND1 | HIS | 6 | 139.754 | 90.942 | 91.094 |
| ATOM | 47 | CD2 | HIS | 6 | 139.693 | 88.811 | 93.310 |
| ATOM | 48 | CE1 | HIS | 6 | 139.643 | 90.946 | 93.098 |
| ATOM | 49 | NE2 | HIS | 6 | 139.620 | 89.950 | 93.959 |
| ATOM | 50 | N | PRO | 7 | 141.170 | 85.479 | 89.513 |
| ATOM | 51 | CA | PRO | 7 | 141.451 | 84.106 | 89.445 |
| ATOM | 52 | C | PRO | 7 | 142.406 | 83.428 | 90.357 |
| ATOM | 53 | O | PRO | 7 | 143.645 | 83.452 | 90.136 |
| ATOM | 54 | CB | PRO | 7 | 141.573 | 83.761 | 87.956 |
| ATOM | 55 | CG | PRO | 7 | 140.747 | 84.851 | 87.278 |
| ATOM | 56 | CD | PRO | 7 | 140.376 | 85.806 | 88.414 |

| ATOM | 57  | N    | ILE | 8  | 142.067 | 82.756 | 91.454 |
|------|-----|------|-----|----|---------|--------|--------|
| ATOM | 58  | HN   | ILE | 8  | 142.795 | 82.371 | 91.906 |
| ATOM | 59  | CA   | ILE | 8  | 140.820 | 82.514 | 92.071 |
| ATOM | 60  | C    | ILE | 8  | 139.579 | 82.532 | 91.276 |
| ATOM | 61  | O    | ILE | 8  | 138.880 | 83.575 | 91.257 |
| ATOM | 62  | CB   | ILE | 8  | 140.613 | 82.952 | 93.545 |
| ATOM | 63  | CG1  | ILE | 8  | 141.247 | 84.268 | 94.032 |
| ATOM | 64  | CG2  | ILE | 8  | 140.957 | 81.795 | 94.485 |
| ATOM | 65  | CD1  | ILE | 8  | 140.175 | 85.340 | 94.261 |
| ATOM | 66  | N    | SER | 9  | 139.281 | 81.419 | 90.612 |
| ATOM | 67  | HN   | SER | 9  | 139.846 | 80.683 | 90.762 |
| ATOM | 68  | CA   | SER | 9  | 138.231 | 81.215 | 89.710 |
| ATOM | 69  | C    | SER | 9  | 137.725 | 79.819 | 89.684 |
| ATOM | 70  | O    | SER | 9  | 138.498 | 78.850 | 89.469 |
| ATOM | 71  | CB   | SER | 9  | 138.671 | 81.688 | 88.315 |
| ATOM | 72  | OG   | SER | 9  | 137.761 | 82.640 | 87.792 |
| ATOM | 73  | HOG  | SER | 9  | 137.609 | 83.392 | 88.401 |
| ATOM | 74  | N    | THR | 10 | 136.472 | 79.421 | 89.873 |
| ATOM | 75  | HN   | THR | 10 | 136.323 | 78.500 | 89.754 |
| ATOM | 76  | CA   | THR | 10 | 135.338 | 80.157 | 90.230 |
| ATOM | 77  | C    | THR | 10 | 134.536 | 80.843 | 89.190 |
| ATOM | 78  | O    | THR | 10 | 133.354 | 80.431 | 89.070 |
| ATOM | 79  | CB   | THR | 10 | 135.308 | 80.619 | 91.706 |
| ATOM | 80  | OG1  | THR | 10 | 134.020 | 80.455 | 92.283 |
| ATOM | 81  | HOG1 | THR | 10 | 133.484 | 81.251 | 92.087 |
| ATOM | 82  | CG2  | THR | 10 | 135.838 | 82.029 | 91.989 |
| ATOM | 83  | N    | GLN | 11 | 135.020 | 81.822 | 88.423 |
| ATOM | 84  | HN   | GLN | 11 | 135.944 | 81.984 | 88.422 |
| ATOM | 85  | CA   | GLN | 11 | 134.342 | 82.697 | 87.567 |
| ATOM | 86  | C    | GLN | 11 | 133.573 | 83.774 | 88.235 |
| ATOM | 87  | O    | GLN | 11 | 132.376 | 83.584 | 88.552 |
| ATOM | 88  | CB   | GLN | 11 | 133.780 | 82.094 | 86.264 |
| ATOM | 89  | CG   | GLN | 11 | 134.033 | 82.999 | 85.042 |
| ATOM | 90  | CD   | GLN | 11 | 135.408 | 82.982 | 84.526 |
| ATOM | 91  | OE1  | GLN | 11 | 136.289 | 83.706 | 85.047 |
| ATOM | 92  | NE2  | GLN | 11 | 135.735 | 82.218 | 83.511 |
| ATOM | 93  | HNE2 | GLN | 11 | 136.618 | 82.217 | 83.192 |
| ATOM | 94  | HNE2 | GLN | 11 | 135.087 | 81.671 | 83.106 |
| ATOM | 95  | N    | SER | 12 | 134.078 | 84.967 | 88.528 |
| ATOM | 96  | HN   | SER | 12 | 133.556 | 85.557 | 89.040 |
| ATOM | 97  | CA   | SER | 12 | 135.333 | 85.440 | 88.146 |
| ATOM | 98  | C    | SER | 12 | 136.184 | 85.763 | 89.313 |
| ATOM | 99  | O    | SER | 12 | 137.126 | 84.940 | 89.430 |
| ATOM | 100 | CB   | SER | 12 | 135.237 | 86.488 | 87.028 |
| ATOM | 101 | OG   | SER | 12 | 136.336 | 86.349 | 86.140 |
| ATOM | 102 | HOG  | SER | 12 | 136.325 | 85.445 | 85.761 |
| ATOM | 103 | N    | PRO | 13 | 136.042 | 86.780 | 90.192 |
| ATOM | 104 | CA   | PRO | 13 | 136.409 | 86.699 | 91.547 |
| ATOM | 105 | C    | PRO | 13 | 135.691 | 85.729 | 92.410 |
| ATOM | 106 | O    | PRO | 13 | 136.371 | 85.208 | 93.333 |
| ATOM | 107 | CB   | PRO | 13 | 136.365 | 88.128 | 92.102 |
| ATOM | 108 | CG   | PRO | 13 | 136.111 | 89.016 | 90.889 |
| ATOM | 109 | CD   | PRO | 13 | 135.526 | 88.035 | 89.876 |
| ATOM | 110 | N    | ASP | 14 | 134.403 | 85.425 | 92.225 |
| ATOM | 111 | HN   | ASP | 14 | 133.941 | 85.896 | 91.558 |
| ATOM | 112 | CA   | ASP | 14 | 133.624 | 84.476 | 92.899 |
| ATOM | 113 | C    | ASP | 14 | 132.476 | 84.002 | 92.090 |
| ATOM | 114 | O    | ASP | 14 | 132.496 | 82.802 | 91.733 |
| ATOM | 115 | CB   | ASP | 14 | 133.243 | 84.950 | 94.313 |
| ATOM | 116 | CG   | ASP | 14 | 132.847 | 83.961 | 95.318 |

-20-

| | | | | | | | |
|---|---|---|---|---|---|---|---|
| ATOM | 117 | OD1 | ASP | 14 | 133.195 | 82.761 | 95.333 |
| ATOM | 118 | OD2 | ASP | 14 | 132.102 | 84.364 | 96.228 |
| ATOM | 119 | N | LEU | 15 | 131.401 | 84.669 | 91.664 |
| ATOM | 120 | HN | LEU | 15 | 130.765 | 84.155 | 91.202 |
| ATOM | 121 | CA | LEU | 15 | 131.087 | 86.026 | 91.806 |
| ATOM | 122 | C | LEU | 15 | 132.080 | 87.008 | 91.291 |
| ATOM | 123 | O | LEU | 15 | 132.652 | 86.804 | 90.192 |
| ATOM | 124 | CB | LEU | 15 | 129.699 | 86.206 | 91.166 |
| ATOM | 125 | CG | LEU | 15 | 128.864 | 87.292 | 91.851 |
| ATOM | 126 | CD1 | LEU | 15 | 128.412 | 88.319 | 90.810 |
| ATOM | 127 | CD2 | LEU | 15 | 127.641 | 86.665 | 92.523 |
| ATOM | 128 | N | GLU | 16 | 132.481 | 88.141 | 91.872 |
| ATOM | 129 | HN | GLU | 16 | 133.174 | 88.581 | 91.413 |
| ATOM | 130 | CA | GLU | 16 | 132.065 | 88.807 | 93.035 |
| ATOM | 131 | C | GLU | 16 | 133.005 | 89.892 | 93.456 |
| ATOM | 132 | O | GLU | 16 | 134.120 | 89.535 | 93.944 |
| ATOM | 133 | CB | GLU | 16 | 131.554 | 87.987 | 94.244 |
| ATOM | 134 | CG | GLU | 16 | 130.229 | 88.426 | 94.900 |
| ATOM | 135 | CD | GLU | 16 | 129.810 | 89.815 | 94.693 |
| ATOM | 136 | OE1 | GLU | 16 | 128.932 | 90.088 | 93.848 |
| ATOM | 137 | OE2 | GLU | 16 | 130.322 | 90.750 | 95.349 |
| ATOM | 138 | N | PRO | 17 | 132.749 | 91.218 | 93.352 |
| ATOM | 139 | CA | PRO | 17 | 133.473 | 92.249 | 93.987 |
| ATOM | 140 | C | PRO | 17 | 133.728 | 92.219 | 95.449 |
| ATOM | 141 | O | PRO | 17 | 134.899 | 92.555 | 95.783 |
| ATOM | 142 | CB | PRO | 17 | 132.865 | 93.586 | 93.541 |
| ATOM | 143 | CG | PRO | 17 | 132.018 | 93.218 | 92.329 |
| ATOM | 144 | CD | PRO | 17 | 131.712 | 91.742 | 92.575 |
| ATOM | 145 | N | ILE | 18 | 132.796 | 91.870 | 96.345 |
| ATOM | 146 | HN | ILE | 18 | 132.002 | 91.504 | 96.000 |
| ATOM | 147 | CA | ILE | 18 | 132.843 | 91.993 | 97.754 |
| ATOM | 148 | C | ILE | 18 | 134.088 | 91.636 | 98.463 |
| ATOM | 149 | O | ILE | 18 | 134.605 | 90.492 | 98.334 |
| ATOM | 150 | CB | ILE | 18 | 131.564 | 91.674 | 98.576 |
| ATOM | 151 | CG1 | ILE | 18 | 130.936 | 90.281 | 98.356 |
| ATOM | 152 | CG2 | ILE | 18 | 130.548 | 92.826 | 98.457 |
| ATOM | 153 | CD1 | ILE | 18 | 130.260 | 89.642 | 99.578 |
| ATOM | 154 | N | LEU | 19 | 134.607 | 92.599 | 99.223 |
| ATOM | 155 | HN | LEU | 19 | 134.090 | 93.383 | 99.276 |
| ATOM | 156 | CA | LEU | 19 | 135.802 | 92.638 | 99.955 |
| ATOM | 157 | C | LEU | 19 | 135.769 | 92.273 | 101.386 |
| ATOM | 158 | O | LEU | 19 | 135.996 | 93.185 | 102.210 |
| ATOM | 159 | CB | LEU | 19 | 137.134 | 92.325 | 99.237 |
| ATOM | 160 | CG | LEU | 19 | 137.621 | 93.422 | 98.272 |
| ATOM | 161 | CD1 | LEU | 19 | 138.172 | 94.664 | 98.988 |
| ATOM | 162 | CD2 | LEU | 19 | 138.748 | 92.854 | 97.409 |
| ATOM | 163 | N | ARG | 20 | 135.540 | 91.110 | 101.974 |
| ATOM | 164 | HN | ARG | 20 | 135.629 | 91.095 | 102.909 |
| ATOM | 165 | CA | ARG | 20 | 135.181 | 89.915 | 101.369 |
| ATOM | 166 | C | ARG | 20 | 134.019 | 89.294 | 102.048 |
| ATOM | 167 | O | ARG | 20 | 132.939 | 89.331 | 101.422 |
| ATOM | 168 | CB | ARG | 20 | 136.413 | 89.009 | 101.198 |
| ATOM | 169 | CG | ARG | 20 | 136.187 | 87.996 | 100.074 |
| ATOM | 170 | CD | ARG | 20 | 137.321 | 88.062 | 99.051 |
| ATOM | 171 | NE | ARG | 20 | 137.046 | 88.933 | 97.995 |
| ATOM | 172 | HNE | ARG | 20 | 136.258 | 89.440 | 98.076 |
| ATOM | 173 | CZ | ARG | 20 | 137.774 | 89.123 | 96.896 |
| ATOM | 174 | NH1 | ARG | 20 | 138.935 | 88.588 | 96.566 |
| ATOM | 175 | HNH1 | ARG | 20 | 139.305 | 88.868 | 95.751 |
| ATOM | 176 | HNH1 | ARG | 20 | 139.367 | 87.962 | 97.118 |

| | | | | | | | |
|---|---|---|---|---|---|---|---|
| ATOM | 177 | NH2 | ARG | 20 | 137.328 | 89.947 | 95.979 |
| ATOM | 178 | HNH2 | ARG | 20 | 137.874 | 90.059 | 95.224 |
| ATOM | 179 | HNH2 | ARG | 20 | 136.513 | 90.404 | 96.070 |
| ATOM | 180 | N | HIS | 21 | 133.971 | 88.700 | 103.238 |
| ATOM | 181 | HN | HIS | 21 | 133.147 | 88.348 | 103.520 |
| ATOM | 182 | CA | HIS | 21 | 135.027 | 88.530 | 104.128 |
| ATOM | 183 | C | HIS | 21 | 135.175 | 87.127 | 104.573 |
| ATOM | 184 | O | HIS | 21 | 136.253 | 86.561 | 104.277 |
| ATOM | 185 | CB | HIS | 21 | 135.014 | 89.577 | 105.257 |
| ATOM | 186 | CG | HIS | 21 | 136.366 | 90.019 | 105.617 |
| ATOM | 187 | ND1 | HIS | 21 | 137.078 | 90.937 | 105.017 |
| ATOM | 188 | HND1 | HIS | 21 | 136.805 | 91.441 | 104.272 |
| ATOM | 189 | CD2 | HIS | 21 | 137.129 | 89.533 | 106.668 |
| ATOM | 190 | CE1 | HIS | 21 | 138.238 | 91.045 | 105.620 |
| ATOM | 191 | NE2 | HIS | 21 | 138.268 | 90.188 | 106.619 |
| ATOM | 192 | N | GLY | 22 | 134.339 | 86.344 | 105.242 |
| ATOM | 193 | HN | GLY | 22 | 134.686 | 85.483 | 105.374 |
| ATOM | 194 | CA | GLY | 22 | 133.074 | 86.640 | 105.746 |
| ATOM | 195 | C | GLY | 22 | 131.974 | 86.456 | 104.780 |
| ATOM | 196 | O | GLY | 22 | 131.560 | 87.470 | 104.171 |
| ATOM | 197 | N | ILE | 23 | 131.354 | 85.323 | 104.482 |
| ATOM | 198 | HN | ILE | 23 | 130.708 | 85.349 | 103.799 |
| ATOM | 199 | CA | ILE | 23 | 131.517 | 84.056 | 105.054 |
| ATOM | 200 | C | ILE | 23 | 131.846 | 82.938 | 104.141 |
| ATOM | 201 | O | ILE | 23 | 132.857 | 82.283 | 104.474 |
| ATOM | 202 | CB | ILE | 23 | 130.529 | 83.610 | 106.167 |
| ATOM | 203 | CG1 | ILE | 23 | 129.179 | 84.337 | 106.337 |
| ATOM | 204 | CG2 | ILE | 23 | 131.257 | 83.609 | 107.518 |
| ATOM | 205 | CD1 | ILE | 23 | 128.028 | 83.575 | 105.673 |
| ATOM | 206 | N | GLN | 24 | 131.273 | 82.471 | 103.029 |
| ATOM | 207 | HN | GLN | 24 | 131.598 | 81.629 | 102.774 |
| ATOM | 208 | CA | GLN | 24 | 130.283 | 82.981 | 102.173 |
| ATOM | 209 | C | GLN | 24 | 130.202 | 84.442 | 101.902 |
| ATOM | 210 | O | GLN | 24 | 129.337 | 85.171 | 102.456 |
| ATOM | 211 | CB | GLN | 24 | 128.931 | 82.288 | 102.439 |
| ATOM | 212 | CG | GLN | 24 | 128.644 | 81.061 | 101.555 |
| ATOM | 213 | CD | GLN | 24 | 129.044 | 79.742 | 102.074 |
| ATOM | 214 | OE1 | GLN | 24 | 129.201 | 79.471 | 103.292 |
| ATOM | 215 | NE2 | GLN | 24 | 129.246 | 78.782 | 101.205 |
| ATOM | 216 | HNE2 | GLN | 24 | 129.449 | 77.911 | 101.494 |
| ATOM | 217 | HNE2 | GLN | 24 | 129.188 | 78.977 | 100.287 |
| ATOM | 218 | N | TYR | 25 | 130.968 | 85.166 | 101.103 |
| ATOM | 219 | HN | TYR | 25 | 130.725 | 86.074 | 101.069 |
| ATOM | 220 | CA | TYR | 25 | 132.067 | 84.848 | 100.305 |
| ATOM | 221 | C | TYR | 25 | 133.197 | 84.120 | 100.938 |
| ATOM | 222 | O | TYR | 25 | 133.688 | 84.502 | 102.036 |
| ATOM | 223 | CB | TYR | 25 | 132.499 | 86.262 | 99.881 |
| ATOM | 224 | CG | TYR | 25 | 133.308 | 86.460 | 98.681 |
| ATOM | 225 | CD1 | TYR | 25 | 132.904 | 87.542 | 97.872 |
| ATOM | 226 | CD2 | TYR | 25 | 134.426 | 85.656 | 98.338 |
| ATOM | 227 | CE1 | TYR | 25 | 133.651 | 87.860 | 96.725 |
| ATOM | 228 | CE2 | TYR | 25 | 135.172 | 85.966 | 97.179 |
| ATOM | 229 | CZ | TYR | 25 | 134.770 | 87.069 | 96.396 |
| ATOM | 230 | OH | TYR | 25 | 135.449 | 87.413 | 95.289 |
| ATOM | 231 | HOH | TYR | 25 | 135.079 | 88.161 | 94.777 |
| ATOM | 232 | N | PHE | 26 | 133.785 | 83.042 | 100.434 |
| ATOM | 233 | HN | PHE | 26 | 134.434 | 82.639 | 100.982 |
| ATOM | 234 | CA | PHE | 26 | 133.572 | 82.428 | 99.190 |
| ATOM | 235 | C | PHE | 26 | 132.311 | 81.676 | 98.974 |
| ATOM | 236 | O | PHE | 26 | 131.740 | 81.098 | 99.940 |

-22-

| | | | | | | | |
|---|---|---|---|---|---|---|---|
| ATOM | 237 | CB | PHE | 26 | 134.797 | 81.519 | 98.983 |
| ATOM | 238 | CG | PHE | 26 | 135.646 | 81.851 | 97.835 |
| ATOM | 239 | CD1 | PHE | 26 | 136.516 | 82.972 | 97.866 |
| ATOM | 240 | CD2 | PHE | 26 | 135.597 | 81.021 | 96.688 |
| ATOM | 241 | CE1 | PHE | 26 | 137.349 | 83.258 | 96.755 |
| ATOM | 242 | CE2 | PHE | 26 | 136.423 | 81.300 | 95.572 |
| ATOM | 243 | CZ | PHE | 26 | 137.294 | 82.417 | 95.616 |
| ATOM | 244 | N | ASN | 27 | 131.809 | 81.634 | 97.738 |
| ATOM | 245 | HN | ASN | 27 | 132.286 | 82.081 | 97.065 |
| ATOM | 246 | CA | ASN | 27 | 130.640 | 81.016 | 97.268 |
| ATOM | 247 | C | ASN | 27 | 130.241 | 79.680 | 97.794 |
| ATOM | 248 | O | ASN | 27 | 129.138 | 79.517 | 98.399 |
| ATOM | 249 | CB | ASN | 27 | 129.555 | 82.110 | 97.138 |
| ATOM | 250 | CG | ASN | 27 | 129.087 | 82.331 | 95.767 |
| ATOM | 251 | OD1 | ASN | 27 | 128.029 | 81.791 | 95.374 |
| ATOM | 252 | ND2 | ASN | 27 | 129.764 | 83.100 | 94.950 |
| ATOM | 253 | HND1 | ASN | 27 | 129.471 | 83.245 | 94.069 |
| ATOM | 254 | HND2 | ASN | 27 | 130.549 | 83.501 | 95.273 |
| ATOM | 255 | N | ASN | 28 | 131.080 | 78.657 | 97.601 |
| ATOM | 256 | HN | ASN | 28 | 131.863 | 78.836 | 97.114 |
| ATOM | 257 | CA | ASN | 28 | 130.907 | 77.345 | 98.057 |
| ATOM | 258 | C | ASN | 28 | 132.084 | 76.737 | 98.723 |
| ATOM | 259 | O | ASN | 28 | 131.972 | 76.597 | 99.960 |
| ATOM | 260 | CB | ASN | 28 | 130.176 | 76.464 | 97.024 |
| ATOM | 261 | CG | ASN | 28 | 129.136 | 75.630 | 97.633 |
| ATOM | 262 | OD1 | ASN | 28 | 129.430 | 74.489 | 98.050 |
| ATOM | 263 | ND2 | ASN | 28 | 127.900 | 76.061 | 97.741 |
| ATOM | 264 | HND2 | ASN | 28 | 127.241 | 75.509 | 98.122 |
| ATOM | 265 | HND2 | ASN | 28 | 127.678 | 76.924 | 97.441 |
| ATOM | 266 | N | ASN | 29 | 133.242 | 76.323 | 98.206 |
| ATOM | 267 | HN | ASN | 29 | 133.864 | 75.949 | 98.803 |
| ATOM | 268 | CA | ASN | 29 | 133.575 | 76.417 | 96.854 |
| ATOM | 269 | C | ASN | 29 | 133.758 | 75.144 | 96.122 |
| ATOM | 270 | O | ASN | 29 | 132.816 | 74.832 | 95.360 |
| ATOM | 271 | CB | ASN | 29 | 134.605 | 77.530 | 96.583 |
| ATOM | 272 | CG | ASN | 29 | 134.572 | 78.097 | 95.229 |
| ATOM | 273 | OD1 | ASN | 29 | 135.458 | 77.768 | 94.410 |
| ATOM | 274 | ND2 | ASN | 29 | 133.643 | 78.947 | 94.857 |
| ATOM | 275 | HND2 | ASN | 29 | 133.707 | 79.366 | 94.019 |
| ATOM | 276 | HND2 | ASN | 29 | 132.923 | 79.140 | 95.429 |
| ATOM | 277 | N | THR | 30 | 134.763 | 74.275 | 96.142 |
| ATOM | 278 | HN | THR | 30 | 134.708 | 73.570 | 95.523 |
| ATOM | 279 | CA | THR | 30 | 135.889 | 74.269 | 96.971 |
| ATOM | 280 | C | THR | 30 | 137.118 | 74.919 | 96.455 |
| ATOM | 281 | O | THR | 30 | 137.566 | 74.647 | 95.303 |
| ATOM | 282 | CB | THR | 30 | 136.035 | 72.867 | 97.610 |
| ATOM | 283 | OG1 | THR | 30 | 136.578 | 72.970 | 98.914 |
| ATOM | 284 | HOG1 | THR | 30 | 136.126 | 73.688 | 99.403 |
| ATOM | 285 | CG2 | THR | 30 | 136.784 | 71.770 | 96.831 |
| ATOM | 286 | N | GLN | 31 | 137.702 | 75.794 | 97.270 |
| ATOM | 287 | HN | GLN | 31 | 137.343 | 75.863 | 98.136 |
| ATOM | 288 | CA | GLN | 31 | 138.786 | 76.620 | 96.963 |
| ATOM | 289 | C | GLN | 31 | 139.818 | 76.728 | 98.029 |
| ATOM | 290 | O | GLN | 31 | 140.905 | 76.142 | 97.818 |
| ATOM | 291 | CB | GLN | 31 | 138.223 | 77.963 | 96.452 |
| ATOM | 292 | CG | GLN | 31 | 138.989 | 78.654 | 95.308 |
| ATOM | 293 | CD | GLN | 31 | 139.169 | 77.988 | 94.009 |
| ATOM | 294 | OE1 | GLN | 31 | 140.337 | 77.832 | 93.577 |
| ATOM | 295 | NE2 | GLN | 31 | 138.161 | 77.564 | 93.279 |
| ATOM | 296 | HNE2 | GLN | 31 | 138.314 | 77.186 | 92.432 |

| ATOM | 297 | HNE2 | GLN | 31 | 137.286 | 77.639 | 93.613 |
|------|-----|------|-----|----|---------|--------|--------|
| ATOM | 298 | N    | HIS | 32 | 139.750 | 77.371 | 99.194 |
| ATOM | 299 | HN   | HIS | 32 | 140.540 | 77.577 | 99.657 |
| ATOM | 300 | CA   | HIS | 32 | 138.585 | 77.789 | 99.817 |
| ATOM | 301 | C    | HIS | 32 | 138.424 | 79.236 | 100.011 |
| ATOM | 302 | O    | HIS | 32 | 137.392 | 79.688 | 99.458 |
| ATOM | 303 | CB   | HIS | 32 | 138.288 | 76.977 | 101.091 |
| ATOM | 304 | CG   | HIS | 32 | 137.112 | 76.103 | 100.983 |
| ATOM | 305 | ND1  | HIS | 32 | 136.933 | 75.027 | 101.694 |
| ATOM | 306 | HND1 | HIS | 32 | 137.557 | 74.692 | 102.312 |
| ATOM | 307 | CD2  | HIS | 32 | 136.000 | 76.219 | 100.154 |
| ATOM | 308 | CE1  | HIS | 32 | 135.769 | 74.495 | 101.404 |
| ATOM | 309 | NE2  | HIS | 32 | 135.223 | 75.199 | 100.429 |
| ATOM | 310 | N    | SER | 33 | 139.280 | 80.003 | 100.706 |
| ATOM | 311 | HN   | SER | 33 | 140.128 | 79.622 | 100.837 |
| ATOM | 312 | CA   | SER | 33 | 139.035 | 81.386 | 101.245 |
| ATOM | 313 | C    | SER | 33 | 138.012 | 81.382 | 102.321 |
| ATOM | 314 | O    | SER | 33 | 137.015 | 80.595 | 102.326 |
| ATOM | 315 | CB   | SER | 33 | 138.852 | 82.380 | 100.174 |
| ATOM | 316 | OG   | SER | 33 | 139.751 | 83.468 | 100.337 |
| ATOM | 317 | HOG  | SER | 33 | 139.680 | 83.853 | 101.235 |
| ATOM | 318 | N    | SER | 34 | 138.150 | 82.270 | 103.292 |
| ATOM | 319 | HN   | SER | 34 | 138.767 | 82.961 | 103.141 |
| ATOM | 320 | CA   | SER | 34 | 137.495 | 82.374 | 104.533 |
| ATOM | 321 | C    | SER | 34 | 137.616 | 81.279 | 105.523 |
| ATOM | 322 | O    | SER | 34 | 137.874 | 81.613 | 106.708 |
| ATOM | 323 | CB   | SER | 34 | 136.068 | 82.921 | 104.379 |
| ATOM | 324 | OG   | SER | 34 | 135.800 | 83.871 | 105.397 |
| ATOM | 325 | HOG  | SER | 34 | 135.972 | 84.769 | 105.043 |
| ATOM | 326 | N    | TYR | 35 | 137.451 | 80.018 | 105.138 |
| ATOM | 327 | HN   | TYR | 35 | 137.297 | 79.962 | 104.213 |
| ATOM | 328 | CA   | TYR | 35 | 137.473 | 78.841 | 105.902 |
| ATOM | 329 | C    | TYR | 35 | 138.829 | 78.296 | 106.128 |
| ATOM | 330 | O    | TYR | 35 | 139.580 | 77.993 | 105.155 |
| ATOM | 331 | CB   | TYR | 35 | 136.501 | 77.724 | 105.433 |
| ATOM | 332 | CG   | TYR | 35 | 135.286 | 78.119 | 104.707 |
| ATOM | 333 | CD1  | TYR | 35 | 134.083 | 78.401 | 105.405 |
| ATOM | 334 | CD2  | TYR | 35 | 135.357 | 78.215 | 103.296 |
| ATOM | 335 | CE1  | TYR | 35 | 132.959 | 78.867 | 104.683 |
| ATOM | 336 | CE2  | TYR | 35 | 134.250 | 78.712 | 102.576 |
| ATOM | 337 | CZ   | TYR | 35 | 133.073 | 79.049 | 103.283 |
| ATOM | 338 | OH   | TYR | 35 | 132.045 | 79.552 | 102.571 |
| ATOM | 339 | HOH  | TYR | 35 | 131.144 | 79.645 | 102.943 |
| ATOM | 340 | N    | PHE | 36 | 139.206 | 78.142 | 107.393 |
| ATOM | 341 | HN   | PHE | 36 | 138.622 | 78.474 | 108.052 |
| ATOM | 342 | CA   | PHE | 36 | 140.379 | 77.528 | 107.844 |
| ATOM | 343 | C    | PHE | 36 | 140.230 | 76.070 | 108.056 |
| ATOM | 344 | O    | PHE | 36 | 139.340 | 75.613 | 108.830 |
| ATOM | 345 | CB   | PHE | 36 | 140.974 | 78.329 | 109.022 |
| ATOM | 346 | CG   | PHE | 36 | 142.151 | 77.734 | 109.668 |
| ATOM | 347 | CD1  | PHE | 36 | 143.389 | 77.621 | 108.980 |
| ATOM | 348 | CD2  | PHE | 36 | 142.028 | 77.267 | 111.002 |
| ATOM | 349 | CE1  | PHE | 36 | 144.499 | 77.014 | 109.617 |
| ATOM | 350 | CE2  | PHE | 36 | 143.138 | 76.666 | 111.646 |
| ATOM | 351 | CZ   | PHE | 36 | 144.363 | 76.542 | 110.945 |
| ATOM | 352 | N    | MET | 37 | 141.086 | 75.295 | 107.389 |
| ATOM | 353 | HN   | MET | 37 | 141.749 | 75.742 | 106.894 |
| ATOM | 354 | CA   | MET | 37 | 141.141 | 73.892 | 107.324 |
| ATOM | 355 | C    | MET | 37 | 140.142 | 73.243 | 106.450 |
| ATOM | 356 | O    | MET | 37 | 138.905 | 73.386 | 106.652 |

-24-

| ATOM | 357 | CB | MET | 37 | 141.436 | 73.144 | 108.645 |
|------|-----|-----|-----|-----|---------|--------|---------|
| ATOM | 358 | CG | MET | 37 | 142.856 | 73.370 | 109.192 |
| ATOM | 359 | SD | MET | 37 | 144.093 | 72.637 | 108.154 |
| ATOM | 360 | CE | MET | 37 | 145.619 | 73.083 | 108.932 |
| ATOM | 361 | N | LEU | 38 | 140.642 | 72.515 | 105.453 |
| ATOM | 362 | HN | LEU | 38 | 141.562 | 72.329 | 105.516 |
| ATOM | 363 | CA | LEU | 38 | 140.004 | 71.995 | 104.315 |
| ATOM | 364 | C | LEU | 38 | 139.865 | 72.996 | 103.240 |
| ATOM | 365 | O | LEU | 38 | 139.057 | 73.960 | 103.358 |
| ATOM | 366 | CB | LEU | 38 | 138.798 | 71.052 | 104.532 |
| ATOM | 367 | CG | LEU | 38 | 138.546 | 70.138 | 103.324 |
| ATOM | 368 | CD1 | LEU | 38 | 138.327 | 68.701 | 103.803 |
| ATOM | 369 | CD2 | LEU | 38 | 137.309 | 70.600 | 102.544 |
| ATOM | 370 | N | ASN | 39 | 140.650 | 72.793 | 102.183 |
| ATOM | 371 | HN | ASN | 39 | 141.075 | 71.955 | 102.139 |
| ATOM | 372 | CA | ASN | 39 | 140.928 | 73.684 | 101.135 |
| ATOM | 373 | C | ASN | 39 | 141.672 | 74.931 | 101.479 |
| ATOM | 374 | O | ASN | 39 | 141.846 | 75.256 | 102.694 |
| ATOM | 375 | CB | ASN | 39 | 139.759 | 73.766 | 100.130 |
| ATOM | 376 | CG | ASN | 39 | 139.887 | 72.825 | 99.012 |
| ATOM | 377 | OD1 | ASN | 39 | 139.611 | 71.609 | 99.152 |
| ATOM | 378 | ND2 | ASN | 39 | 140.293 | 73.276 | 97.853 |
| ATOM | 379 | HND2 | ASN | 39 | 140.380 | 72.699 | 97.115 |
| ATOM | 380 | HND2 | ASN | 39 | 140.495 | 74.190 | 97.778 |
| ATOM | 381 | N | GLU | 40 | 142.170 | 75.707 | 100.510 |
| ATOM | 382 | HN | GLU | 40 | 141.820 | 75.628 | 99.642 |
| ATOM | 383 | CA | GLU | 40 | 143.189 | 76.661 | 100.667 |
| ATOM | 384 | C | GLU | 40 | 142.876 | 78.012 | 100.139 |
| ATOM | 385 | O | GLU | 40 | 141.946 | 78.639 | 100.732 |
| ATOM | 386 | CB | GLU | 40 | 144.626 | 76.089 | 100.521 |
| ATOM | 387 | CG | GLU | 40 | 144.999 | 75.298 | 99.246 |
| ATOM | 388 | CD | GLU | 40 | 145.029 | 76.034 | 97.977 |
| ATOM | 389 | OE1 | GLU | 40 | 145.691 | 77.083 | 97.810 |
| ATOM | 390 | OE2 | GLU | 40 | 144.379 | 75.621 | 96.995 |
| ATOM | 391 | N | VAL | 41 | 143.532 | 78.535 | 99.103 |
| ATOM | 392 | HN | VAL | 41 | 144.202 | 78.005 | 98.713 |
| ATOM | 393 | CA | VAL | 41 | 143.363 | 79.793 | 98.503 |
| ATOM | 394 | C | VAL | 41 | 144.596 | 80.539 | 98.178 |
| ATOM | 395 | O | VAL | 41 | 144.516 | 81.775 | 98.377 |
| ATOM | 396 | CB | VAL | 41 | 142.375 | 79.923 | 97.317 |
| ATOM | 397 | CG1 | VAL | 41 | 142.368 | 78.841 | 96.231 |
| ATOM | 398 | CG2 | VAL | 41 | 140.957 | 80.270 | 97.770 |
| ATOM | 399 | N | LYS | 42 | 145.710 | 79.974 | 97.706 |
| ATOM | 400 | HN | LYS | 42 | 145.715 | 79.035 | 97.677 |
| ATOM | 401 | CA | LYS | 42 | 146.854 | 80.649 | 97.263 |
| ATOM | 402 | C | LYS | 42 | 146.849 | 80.925 | 95.802 |
| ATOM | 403 | O | LYS | 42 | 147.573 | 80.280 | 94.982 |
| ATOM | 404 | CB | LYS | 42 | 148.078 | 79.949 | 97.878 |
| ATOM | 405 | CG | LYS | 42 | 149.294 | 80.876 | 97.933 |
| ATOM | 406 | CD | LYS | 42 | 150.150 | 80.498 | 99.147 |
| ATOM | 407 | CE | LYS | 42 | 151.389 | 81.388 | 99.301 |
| ATOM | 408 | NZ | LYS | 42 | 151.084 | 82.506 | 100.186 |
| ATOM | 409 | HNZ | LYS | 42 | 151.908 | 83.088 | 100.328 |
| ATOM | 410 | HNZ | LYS | 42 | 150.318 | 83.053 | 99.795 |
| ATOM | 411 | HNZ | LYS | 42 | 150.776 | 82.167 | 101.096 |
| ATOM | 412 | N | ARG | 43 | 146.029 | 81.891 | 95.391 |
| ATOM | 413 | HN | ARG | 43 | 145.563 | 82.360 | 96.057 |
| ATOM | 414 | CA | ARG | 43 | 145.783 | 82.270 | 94.067 |
| ATOM | 415 | C | ARG | 43 | 145.941 | 83.710 | 93.774 |
| ATOM | 416 | O | ARG | 43 | 146.565 | 83.966 | 92.700 |

| | | | | | | | |
|---|---|---|---|---|---|---|---|
| ATOM | 417 | CB | ARG | 43 | 144.493 | 81.593 | 93.565 |
| ATOM | 418 | CG | ARG | 43 | 144.667 | 80.731 | 92.296 |
| ATOM | 419 | CD | ARG | 43 | 145.515 | 79.450 | 92.419 |
| ATOM | 420 | NE | ARG | 43 | 144.819 | 78.321 | 92.876 |
| ATOM | 421 | HNE | ARG | 43 | 144.190 | 77.961 | 92.276 |
| ATOM | 422 | CZ | ARG | 43 | 144.930 | 77.691 | 94.050 |
| ATOM | 423 | NH1 | ARG | 43 | 144.192 | 76.632 | 94.273 |
| ATOM | 424 | HNH1 | ARG | 43 | 144.241 | 76.238 | 95.125 |
| ATOM | 425 | HNH1 | ARG | 43 | 143.632 | 76.280 | 93.606 |
| ATOM | 426 | NH2 | ARG | 43 | 145.712 | 78.012 | 95.061 |
| ATOM | 427 | HNH2 | ARG | 43 | 145.667 | 77.548 | 95.875 |
| ATOM | 428 | HNH2 | ARG | 43 | 146.325 | 78.721 | 94.982 |
| ATOM | 429 | N | ALA | 44 | 145.479 | 84.678 | 94.591 |
| ATOM | 430 | HN | ALA | 44 | 144.962 | 84.425 | 95.333 |
| ATOM | 431 | CA | ALA | 44 | 145.688 | 86.067 | 94.498 |
| ATOM | 432 | C | ALA | 44 | 147.067 | 86.550 | 94.790 |
| ATOM | 433 | O | ALA | 44 | 147.221 | 87.612 | 95.453 |
| ATOM | 434 | CB | ALA | 44 | 144.968 | 86.688 | 93.286 |
| ATOM | 435 | N | GLN | 45 | 148.104 | 85.836 | 94.343 |
| ATOM | 436 | HN | GLN | 45 | 147.809 | 85.154 | 93.770 |
| ATOM | 437 | CA | GLN | 45 | 149.480 | 85.932 | 94.590 |
| ATOM | 438 | C | GLN | 45 | 150.316 | 85.364 | 93.497 |
| ATOM | 439 | O | GLN | 45 | 150.011 | 84.303 | 92.896 |
| ATOM | 440 | CB | GLN | 45 | 149.762 | 85.172 | 95.898 |
| ATOM | 441 | CG | GLN | 45 | 150.625 | 86.019 | 96.841 |
| ATOM | 442 | CD | GLN | 45 | 151.572 | 85.288 | 97.693 |
| ATOM | 443 | OE1 | GLN | 45 | 152.328 | 84.374 | 97.270 |
| ATOM | 444 | NE2 | GLN | 45 | 151.624 | 85.626 | 98.949 |
| ATOM | 445 | HNE2 | GLN | 45 | 152.224 | 85.197 | 99.531 |
| ATOM | 446 | HNE2 | GLN | 45 | 151.050 | 86.304 | 99.254 |
| ATOM | 447 | N | ARG | 46 | 151.447 | 85.846 | 93.006 |
| ATOM | 448 | HN | ARG | 46 | 151.822 | 85.346 | 92.303 |
| ATOM | 449 | CA | ARG | 46 | 152.162 | 86.988 | 93.377 |
| ATOM | 450 | C | ARG | 46 | 152.387 | 87.943 | 92.263 |
| ATOM | 451 | O | ARG | 46 | 152.662 | 87.539 | 91.100 |
| ATOM | 452 | CB | ARG | 46 | 153.510 | 86.577 | 93.996 |
| ATOM | 453 | CG | ARG | 46 | 153.509 | 86.947 | 95.480 |
| ATOM | 454 | CD | ARG | 46 | 154.910 | 87.056 | 96.087 |
| ATOM | 455 | NE | ARG | 46 | 154.850 | 87.323 | 97.461 |
| ATOM | 456 | HNE | ARG | 46 | 155.049 | 86.602 | 98.030 |
| ATOM | 457 | CZ | ARG | 46 | 154.554 | 88.453 | 98.107 |
| ATOM | 458 | NH1 | ARG | 46 | 154.699 | 88.390 | 99.405 |
| ATOM | 459 | HNH1 | ARG | 46 | 154.707 | 89.158 | 99.945 |
| ATOM | 460 | HNH1 | ARG | 46 | 154.795 | 87.541 | 99.797 |
| ATOM | 461 | NH2 | ARG | 46 | 154.136 | 89.600 | 97.608 |
| ATOM | 462 | HNH2 | ARG | 46 | 153.825 | 90.258 | 98.200 |
| ATOM | 463 | HNH2 | ARG | 46 | 154.137 | 89.749 | 96.679 |
| ATOM | 464 | N | GLN | 47 | 152.324 | 89.267 | 92.366 |
| ATOM | 465 | HN | GLN | 47 | 152.510 | 89.734 | 91.573 |
| ATOM | 466 | CA | GLN | 47 | 152.028 | 90.085 | 93.463 |
| ATOM | 467 | C | GLN | 47 | 153.123 | 90.713 | 94.230 |
| ATOM | 468 | O | GLN | 47 | 154.046 | 90.022 | 94.728 |
| ATOM | 469 | CB | GLN | 47 | 150.651 | 89.911 | 94.138 |
| ATOM | 470 | CG | GLN | 47 | 149.786 | 91.189 | 94.070 |
| ATOM | 471 | CD | GLN | 47 | 149.820 | 91.966 | 92.820 |
| ATOM | 472 | OE1 | GLN | 47 | 149.488 | 91.455 | 91.727 |
| ATOM | 473 | NE2 | GLN | 47 | 150.204 | 93.219 | 92.829 |
| ATOM | 474 | HNE1 | GLN | 47 | 150.365 | 93.652 | 92.011 |
| ATOM | 475 | HNE2 | GLN | 47 | 150.315 | 93.670 | 93.645 |
| ATOM | 476 | N | VAL | 48 | 153.051 | 92.037 | 94.339 |

-26-

| | | | | | | | |
|---|---|---|---|---|---|---|---|
| ATOM | 477 | HN | VAL | 48 | 152.248 | 92.413 | 94.027 |
| ATOM | 478 | CA | VAL | 48 | 153.971 | 92.965 | 94.834 |
| ATOM | 479 | C | VAL | 48 | 155.354 | 92.913 | 94.294 |
| ATOM | 480 | O | VAL | 48 | 156.266 | 92.335 | 94.928 |
| ATOM | 481 | CB | VAL | 48 | 153.623 | 93.614 | 96.196 |
| ATOM | 482 | CG1 | VAL | 48 | 154.471 | 93.214 | 97.409 |
| ATOM | 483 | CG2 | VAL | 48 | 153.630 | 95.144 | 96.091 |
| ATOM | 484 | N | VAL | 49 | 155.727 | 93.448 | 93.141 |
| ATOM | 485 | HN | VAL | 49 | 156.647 | 93.472 | 92.955 |
| ATOM | 486 | CA | VAL | 49 | 154.859 | 93.972 | 92.169 |
| ATOM | 487 | C | VAL | 49 | 154.543 | 92.972 | 91.137 |
| ATOM | 488 | O | VAL | 49 | 153.360 | 92.536 | 91.161 |
| ATOM | 489 | CB | VAL | 49 | 154.976 | 95.419 | 91.630 |
| ATOM | 490 | CG1 | VAL | 49 | 153.749 | 96.222 | 92.074 |
| ATOM | 491 | CG2 | VAL | 49 | 156.243 | 96.243 | 91.918 |
| ATOM | 492 | N | ALA | 50 | 155.463 | 92.564 | 90.258 |
| ATOM | 493 | HN | ALA | 50 | 156.289 | 93.012 | 90.277 |
| ATOM | 494 | CA | ALA | 50 | 155.333 | 91.538 | 89.318 |
| ATOM | 495 | C | ALA | 50 | 154.799 | 90.256 | 89.859 |
| ATOM | 496 | O | ALA | 50 | 155.419 | 89.611 | 90.748 |
| ATOM | 497 | CB | ALA | 50 | 156.618 | 91.406 | 88.487 |
| ATOM | 498 | N | GLY | 51 | 153.653 | 89.700 | 89.479 |
| ATOM | 499 | HN | GLY | 51 | 153.370 | 88.950 | 89.968 |
| ATOM | 500 | CA | GLY | 51 | 152.818 | 90.108 | 88.442 |
| ATOM | 501 | C | GLY | 51 | 151.376 | 90.188 | 88.756 |
| ATOM | 502 | O | GLY | 51 | 150.762 | 89.134 | 89.039 |
| ATOM | 503 | N | LEU | 52 | 150.627 | 91.284 | 88.751 |
| ATOM | 504 | HN | LEU | 52 | 149.698 | 91.169 | 88.830 |
| ATOM | 505 | CA | LEU | 52 | 151.046 | 92.609 | 88.628 |
| ATOM | 506 | C | LEU | 52 | 150.248 | 93.585 | 89.404 |
| ATOM | 507 | O | LEU | 52 | 150.896 | 94.359 | 90.151 |
| ATOM | 508 | CB | LEU | 52 | 151.123 | 92.971 | 87.128 |
| ATOM | 509 | CG | LEU | 52 | 152.036 | 94.166 | 86.828 |
| ATOM | 510 | CD1 | LEU | 52 | 153.433 | 93.688 | 86.419 |
| ATOM | 511 | CD2 | LEU | 52 | 151.423 | 94.967 | 85.678 |
| ATOM | 512 | N | ASN | 53 | 148.917 | 93.641 | 89.309 |
| ATOM | 513 | HN | ASN | 53 | 148.488 | 92.853 | 89.028 |
| ATOM | 514 | CA | ASN | 53 | 148.093 | 94.745 | 89.564 |
| ATOM | 515 | C | ASN | 53 | 147.801 | 94.952 | 91.001 |
| ATOM | 516 | O | ASN | 53 | 148.401 | 95.900 | 91.567 |
| ATOM | 517 | CB | ASN | 53 | 146.845 | 94.727 | 88.642 |
| ATOM | 518 | CG | ASN | 53 | 147.036 | 94.581 | 87.190 |
| ATOM | 519 | OD1 | ASN | 53 | 147.042 | 95.597 | 86.463 |
| ATOM | 520 | ND2 | ASN | 53 | 147.198 | 93.396 | 86.645 |
| ATOM | 521 | HND2 | ASN | 53 | 147.254 | 93.301 | 85.711 |
| ATOM | 522 | HND2 | ASN | 53 | 147.261 | 92.645 | 87.206 |
| ATOM | 523 | N | PHE | 54 | 146.942 | 94.155 | 91.638 |
| ATOM | 524 | HN | PHE | 54 | 146.501 | 93.529 | 91.093 |
| ATOM | 525 | CA | PHE | 54 | 146.599 | 94.102 | 92.995 |
| ATOM | 526 | C | PHE | 54 | 146.374 | 92.721 | 93.494 |
| ATOM | 527 | O | PHE | 54 | 146.797 | 92.461 | 94.650 |
| ATOM | 528 | CB | PHE | 54 | 145.512 | 95.128 | 93.394 |
| ATOM | 529 | CG | PHE | 54 | 144.115 | 94.801 | 93.085 |
| ATOM | 530 | CD1 | PHE | 54 | 143.351 | 94.023 | 93.997 |
| ATOM | 531 | CD2 | PHE | 54 | 143.536 | 95.270 | 91.877 |
| ATOM | 532 | CE1 | PHE | 54 | 142.006 | 93.701 | 93.695 |
| ATOM | 533 | CE2 | PHE | 54 | 142.188 | 94.955 | 91.576 |
| ATOM | 534 | CZ | PHE | 54 | 141.435 | 94.169 | 92.485 |
| ATOM | 535 | N | ARG | 55 | 145.754 | 91.798 | 92.744 |
| ATOM | 536 | HN | ARG | 55 | 145.415 | 92.113 | 91.926 |

| | | | | | | | |
|---|---|---|---|---|---|---|---|
| ATOM | 537 | CA | ARG | 55 | 145.537 | 90.436 | 92.986 |
| ATOM | 538 | C | ARG | 55 | 144.580 | 90.132 | 94.084 |
| ATOM | 539 | O | ARG | 55 | 143.398 | 90.537 | 93.901 |
| ATOM | 540 | CB | ARG | 55 | 146.852 | 89.630 | 92.884 |
| ATOM | 541 | CG | ARG | 55 | 147.177 | 89.046 | 91.506 |
| ATOM | 542 | CD | ARG | 55 | 148.219 | 87.952 | 91.754 |
| ATOM | 543 | NE | ARG | 55 | 148.909 | 87.555 | 90.613 |
| ATOM | 544 | HNE | ARG | 55 | 149.460 | 88.186 | 90.187 |
| ATOM | 545 | CZ | ARG | 55 | 148.931 | 86.379 | 89.997 |
| ATOM | 546 | NH1 | ARG | 55 | 149.741 | 86.395 | 88.969 |
| ATOM | 547 | HNH1 | ARG | 55 | 149.875 | 85.643 | 88.421 |
| ATOM | 548 | HNH1 | ARG | 55 | 150.178 | 87.212 | 88.819 |
| ATOM | 549 | NH2 | ARG | 55 | 148.287 | 85.251 | 90.261 |
| ATOM | 550 | HNH2 | ARG | 55 | 148.379 | 84.530 | 89.665 |
| ATOM | 551 | HNH2 | ARG | 55 | 147.742 | 85.146 | 91.019 |
| ATOM | 552 | N | ILE | 56 | 144.925 | 89.465 | 95.192 |
| ATOM | 553 | HN | ILE | 56 | 145.765 | 89.043 | 95.207 |
| ATOM | 554 | CA | ILE | 56 | 144.194 | 89.281 | 96.368 |
| ATOM | 555 | C | ILE | 56 | 143.197 | 88.191 | 96.365 |
| ATOM | 556 | O | ILE | 56 | 142.189 | 88.235 | 95.611 |
| ATOM | 557 | CB | ILE | 56 | 143.948 | 90.562 | 97.211 |
| ATOM | 558 | CG1 | ILE | 56 | 144.230 | 90.343 | 98.706 |
| ATOM | 559 | CG2 | ILE | 56 | 142.570 | 91.230 | 97.057 |
| ATOM | 560 | CD1 | ILE | 56 | 145.714 | 90.518 | 99.053 |
| ATOM | 561 | N | THR | 57 | 143.433 | 87.190 | 97.203 |
| ATOM | 562 | HN | THR | 57 | 144.297 | 87.119 | 97.566 |
| ATOM | 563 | CA | THR | 57 | 142.482 | 86.239 | 97.602 |
| ATOM | 564 | C | THR | 57 | 141.553 | 86.816 | 98.607 |
| ATOM | 565 | O | THR | 57 | 140.334 | 86.663 | 98.331 |
| ATOM | 566 | CB | THR | 57 | 142.965 | 84.799 | 97.906 |
| ATOM | 567 | OG1 | THR | 57 | 144.086 | 84.302 | 97.180 |
| ATOM | 568 | HOG1 | THR | 57 | 144.282 | 83.418 | 97.554 |
| ATOM | 569 | CG2 | THR | 57 | 141.857 | 83.778 | 97.629 |
| ATOM | 570 | N | TYR | 58 | 141.970 | 87.461 | 99.711 |
| ATOM | 571 | HN | TYR | 58 | 142.887 | 87.380 | 99.897 |
| ATOM | 572 | CA | TYR | 58 | 141.249 | 88.251 | 100.623 |
| ATOM | 573 | C | TYR | 58 | 140.469 | 87.500 | 101.632 |
| ATOM | 574 | O | TYR | 58 | 139.305 | 87.095 | 101.368 |
| ATOM | 575 | CB | TYR | 58 | 140.535 | 89.442 | 99.933 |
| ATOM | 576 | CG | TYR | 58 | 140.310 | 90.675 | 100.694 |
| ATOM | 577 | CD1 | TYR | 58 | 139.472 | 90.690 | 101.839 |
| ATOM | 578 | CD2 | TYR | 58 | 140.949 | 91.856 | 100.239 |
| ATOM | 579 | CE1 | TYR | 58 | 139.256 | 91.909 | 102.520 |
| ATOM | 580 | CE2 | TYR | 58 | 140.730 | 93.076 | 100.920 |
| ATOM | 581 | CZ | TYR | 58 | 139.884 | 93.087 | 102.054 |
| ATOM | 582 | OH | TYR | 58 | 139.669 | 94.246 | 102.713 |
| ATOM | 583 | HOH | TYR | 58 | 139.087 | 94.255 | 103.502 |
| ATOM | 584 | N | SER | 59 | 141.064 | 87.289 | 102.806 |
| ATOM | 585 | HN | SER | 59 | 141.931 | 87.641 | 102.891 |
| ATOM | 586 | CA | SER | 59 | 140.573 | 86.612 | 103.934 |
| ATOM | 587 | C | SER | 59 | 140.383 | 85.146 | 103.820 |
| ATOM | 588 | O | SER | 59 | 139.641 | 84.650 | 102.946 |
| ATOM | 589 | CB | SER | 59 | 139.450 | 87.337 | 104.691 |
| ATOM | 590 | OG | SER | 59 | 139.991 | 87.983 | 105.833 |
| ATOM | 591 | HOG | SER | 59 | 139.394 | 88.709 | 106.111 |
| ATOM | 592 | N | ILE | 60 | 140.959 | 84.231 | 104.585 |
| ATOM | 593 | HN | ILE | 60 | 140.688 | 83.342 | 104.446 |
| ATOM | 594 | CA | ILE | 60 | 141.930 | 84.432 | 105.577 |
| ATOM | 595 | C | ILE | 60 | 143.186 | 85.009 | 105.033 |
| ATOM | 596 | O | ILE | 60 | 143.506 | 86.114 | 105.526 |

| ATOM | 597 | CB | ILE | 60 | 142.188 | 83.299 | 106.612 |
|------|-----|------|------|----|---------|--------|---------|
| ATOM | 598 | CG1 | ILE | 60 | 141.262 | 82.065 | 106.678 |
| ATOM | 599 | CG2 | ILE | 60 | 142.180 | 83.923 | 108.012 |
| ATOM | 600 | CD1 | ILE | 60 | 141.691 | 80.932 | 105.738 |
| ATOM | 601 | N | VAL | 61 | 143.990 | 84.508 | 104.092 |
| ATOM | 602 | HN | VAL | 61 | 144.694 | 85.046 | 103.778 |
| ATOM | 603 | CA | VAL | 61 | 143.866 | 83.233 | 103.510 |
| ATOM | 604 | C | VAL | 61 | 144.933 | 82.321 | 103.997 |
| ATOM | 605 | O | VAL | 61 | 144.858 | 81.945 | 105.194 |
| ATOM | 606 | CB | VAL | 61 | 143.524 | 83.146 | 101.995 |
| ATOM | 607 | CG1 | VAL | 61 | 142.593 | 81.959 | 101.730 |
| ATOM | 608 | CG2 | VAL | 61 | 142.931 | 84.361 | 101.264 |
| ATOM | 609 | N | GLN | 62 | 145.991 | 81.806 | 103.388 |
| ATOM | 610 | HN | GLN | 62 | 146.626 | 81.425 | 103.968 |
| ATOM | 611 | CA | GLN | 62 | 146.321 | 81.715 | 102.032 |
| ATOM | 612 | C | GLN | 62 | 146.880 | 80.380 | 101.722 |
| ATOM | 613 | O | GLN | 62 | 146.326 | 79.756 | 100.784 |
| ATOM | 614 | CB | GLN | 62 | 147.141 | 82.893 | 101.478 |
| ATOM | 615 | CG | GLN | 62 | 146.653 | 83.199 | 100.050 |
| ATOM | 616 | CD | GLN | 62 | 147.488 | 84.000 | 99.146 |
| ATOM | 617 | OE1 | GLN | 62 | 148.739 | 83.998 | 99.205 |
| ATOM | 618 | NE2 | GLN | 62 | 146.910 | 84.742 | 98.230 |
| ATOM | 619 | HNE2 | GLN | 62 | 147.419 | 85.358 | 97.736 |
| ATOM | 620 | HNE2 | GLN | 62 | 145.991 | 84.661 | 98.053 |
| ATOM | 621 | N | THR | 63 | 147.908 | 79.862 | 102.406 |
| ATOM | 622 | HN | THR | 63 | 148.591 | 80.465 | 102.642 |
| ATOM | 623 | CA | THR | 63 | 148.058 | 78.522 | 102.813 |
| ATOM | 624 | C | THR | 63 | 146.903 | 78.038 | 103.616 |
| ATOM | 625 | O | THR | 63 | 145.751 | 77.930 | 103.110 |
| ATOM | 626 | CB | THR | 63 | 148.728 | 77.616 | 101.748 |
| ATOM | 627 | OG1 | THR | 63 | 150.084 | 78.024 | 101.556 |
| ATOM | 628 | HOG1 | THR | 63 | 150.436 | 78.356 | 102.407 |
| ATOM | 629 | CG2 | THR | 63 | 148.785 | 76.117 | 102.079 |
| ATOM | 630 | N | ASN | 64 | 147.124 | 77.730 | 104.886 |
| ATOM | 631 | HN | ASN | 64 | 148.006 | 77.524 | 105.135 |
| ATOM | 632 | CA | ASN | 64 | 146.171 | 77.688 | 105.911 |
| ATOM | 633 | C | ASN | 64 | 146.610 | 78.441 | 107.111 |
| ATOM | 634 | O | ASN | 64 | 145.853 | 79.364 | 107.496 |
| ATOM | 635 | CB | ASN | 64 | 145.574 | 76.288 | 106.179 |
| ATOM | 636 | CG | ASN | 64 | 144.288 | 76.067 | 105.498 |
| ATOM | 637 | OD1 | ASN | 64 | 143.234 | 76.594 | 105.928 |
| ATOM | 638 | ND2 | ASN | 64 | 144.231 | 75.312 | 104.425 |
| ATOM | 639 | HND2 | ASN | 64 | 143.435 | 75.247 | 103.928 |
| ATOM | 640 | HND2 | ASN | 64 | 144.993 | 74.836 | 104.149 |
| ATOM | 641 | N | CYS | 65 | 147.704 | 78.291 | 107.852 |
| ATOM | 642 | HN | CYS | 65 | 147.807 | 78.953 | 108.509 |
| ATOM | 643 | CA | CYS | 65 | 148.662 | 77.276 | 107.727 |
| ATOM | 644 | C | CYS | 65 | 149.755 | 77.580 | 106.785 |
| ATOM | 645 | O | CYS | 65 | 149.757 | 76.878 | 105.740 |
| ATOM | 646 | CB | CYS | 65 | 149.191 | 76.684 | 109.046 |
| ATOM | 647 | SG | CYS | 65 | 147.981 | 75.852 | 110.043 |
| ATOM | 648 | N | SER | 66 | 150.671 | 78.523 | 107.023 |
| ATOM | 649 | CA | SER | 66 | 151.821 | 78.916 | 106.322 |
| ATOM | 650 | C | SER | 66 | 151.618 | 79.632 | 105.048 |
| ATOM | 651 | O | SER | 66 | 151.071 | 79.038 | 104.073 |
| ATOM | 652 | CB | SER | 66 | 152.894 | 77.809 | 106.255 |
| ATOM | 653 | OG | SER | 66 | 154.197 | 78.343 | 106.052 |
| ATOM | 654 | HOG | SER | 66 | 154.439 | 78.916 | 106.808 |
| ATOM | 655 | N | LYS | 67 | 152.041 | 80.894 | 105.003 |
| ATOM | 656 | HN | LYS | 67 | 152.283 | 81.307 | 105.813 |

| ATOM | 657 | CA | LYS | 67 | 152.161 | 81.641 | 103.831 |
|------|-----|------|------|----|---------|--------|---------|
| ATOM | 658 | C | LYS | 67 | 150.997 | 82.423 | 103.368 |
| ATOM | 659 | O | LYS | 67 | 150.085 | 81.740 | 102.848 |
| ATOM | 660 | CB | LYS | 67 | 153.576 | 82.179 | 103.596 |
| ATOM | 661 | CG | LYS | 67 | 154.216 | 81.366 | 102.467 |
| ATOM | 662 | CD | LYS | 67 | 155.545 | 82.014 | 102.087 |
| ATOM | 663 | CE | LYS | 67 | 155.734 | 82.000 | 100.571 |
| ATOM | 664 | NZ | LYS | 67 | 156.348 | 83.253 | 100.145 |
| ATOM | 665 | HNZ1 | LYS | 67 | 155.739 | 84.042 | 100.354 |
| ATOM | 666 | HNZ2 | LYS | 67 | 156.498 | 83.219 | 99.137 |
| ATOM | 667 | HNZ3 | LYS | 67 | 157.253 | 83.335 | 100.607 |
| ATOM | 668 | N | GLU | 68 | 150.729 | 83.723 | 103.389 |
| ATOM | 669 | HN | GLU | 68 | 149.913 | 83.970 | 102.992 |
| ATOM | 670 | CA | GLU | 68 | 151.484 | 84.770 | 103.918 |
| ATOM | 671 | C | GLU | 68 | 150.720 | 85.384 | 105.031 |
| ATOM | 672 | O | GLU | 68 | 151.049 | 85.037 | 106.183 |
| ATOM | 673 | CB | GLU | 68 | 151.934 | 85.753 | 102.816 |
| ATOM | 674 | CG | GLU | 68 | 153.444 | 85.722 | 102.523 |
| ATOM | 675 | CD | GLU | 68 | 153.843 | 85.175 | 101.220 |
| ATOM | 676 | OE1 | GLU | 68 | 154.693 | 85.730 | 100.495 |
| ATOM | 677 | OE2 | GLU | 68 | 153.381 | 84.119 | 100.743 |
| ATOM | 678 | N | ASN | 69 | 149.711 | 86.252 | 105.036 |
| ATOM | 679 | HN | ASN | 69 | 149.369 | 86.472 | 105.883 |
| ATOM | 680 | CA | ASN | 69 | 149.084 | 86.887 | 103.962 |
| ATOM | 681 | C | ASN | 69 | 148.395 | 88.127 | 104.368 |
| ATOM | 682 | O | ASN | 69 | 148.699 | 89.117 | 103.652 |
| ATOM | 683 | CB | ASN | 69 | 148.284 | 85.932 | 103.035 |
| ATOM | 684 | CG | ASN | 69 | 147.082 | 86.406 | 102.339 |
| ATOM | 685 | OD1 | ASN | 69 | 145.976 | 86.180 | 102.865 |
| ATOM | 686 | ND2 | ASN | 69 | 147.125 | 87.046 | 101.194 |
| ATOM | 687 | HND2 | ASN | 69 | 146.325 | 87.336 | 100.795 |
| ATOM | 688 | HND2 | ASN | 69 | 147.945 | 87.217 | 100.769 |
| ATOM | 689 | N | PHE | 70 | 147.526 | 88.206 | 105.387 |
| ATOM | 690 | HN | PHE | 70 | 147.501 | 87.547 | 106.055 |
| ATOM | 691 | CA | PHE | 70 | 146.599 | 89.228 | 105.544 |
| ATOM | 692 | C | PHE | 70 | 146.632 | 89.940 | 106.840 |
| ATOM | 693 | O | PHE | 70 | 147.156 | 91.065 | 106.791 |
| ATOM | 694 | CB | PHE | 70 | 145.252 | 88.698 | 105.035 |
| ATOM | 695 | CG | PHE | 70 | 144.386 | 89.689 | 104.407 |
| ATOM | 696 | CD1 | PHE | 70 | 143.280 | 90.188 | 105.138 |
| ATOM | 697 | CD2 | PHE | 70 | 144.651 | 90.131 | 103.084 |
| ATOM | 698 | CE1 | PHE | 70 | 142.418 | 91.137 | 104.542 |
| ATOM | 699 | CE2 | PHE | 70 | 143.798 | 91.088 | 102.487 |
| ATOM | 700 | CZ | PHE | 70 | 142.694 | 91.579 | 103.226 |
| ATOM | 701 | N | LEU | 71 | 146.212 | 89.628 | 108.060 |
| ATOM | 702 | HN | LEU | 71 | 146.378 | 90.285 | 108.710 |
| ATOM | 703 | CA | LEU | 71 | 145.565 | 88.489 | 108.541 |
| ATOM | 704 | C | LEU | 71 | 146.377 | 87.305 | 108.854 |
| ATOM | 705 | O | LEU | 71 | 147.034 | 86.694 | 107.961 |
| ATOM | 706 | CB | LEU | 71 | 144.125 | 88.221 | 108.061 |
| ATOM | 707 | CG | LEU | 71 | 143.093 | 88.581 | 109.134 |
| ATOM | 708 | CD1 | LEU | 71 | 141.981 | 89.429 | 108.512 |
| ATOM | 709 | CD2 | LEU | 71 | 142.479 | 87.306 | 109.717 |
| ATOM | 710 | N | PHE | 72 | 146.333 | 86.971 | 110.140 |
| ATOM | 711 | HN | PHE | 72 | 145.821 | 87.541 | 110.685 |
| ATOM | 712 | CA | PHE | 72 | 146.932 | 85.896 | 110.795 |
| ATOM | 713 | C | PHE | 72 | 146.780 | 84.582 | 110.141 |
| ATOM | 714 | O | PHE | 72 | 145.649 | 84.077 | 109.873 |
| ATOM | 715 | CB | PHE | 72 | 146.445 | 85.920 | 112.258 |
| ATOM | 716 | CG | PHE | 72 | 147.494 | 86.159 | 113.257 |

-30-

| ATOM | 717 | CD1 | PHE | 72 | 148.218 | 87.382 | 113.299 |
|------|-----|-----|-----|----|---------|--------|---------|
| ATOM | 718 | CD2 | PHE | 72 | 147.771 | 85.134 | 114.197 |
| ATOM | 719 | CE1 | PHE | 72 | 149.223 | 87.574 | 114.279 |
| ATOM | 720 | CE2 | PHE | 72 | 148.776 | 85.318 | 115.177 |
| ATOM | 721 | CZ | PHE | 72 | 149.495 | 86.539 | 115.208 |
| ATOM | 722 | N | LEU | 73 | 147.921 | 83.972 | 109.848 |
| ATOM | 723 | HN | LEU | 73 | 148.717 | 84.370 | 110.150 |
| ATOM | 724 | CA | LEU | 73 | 148.059 | 82.791 | 109.123 |
| ATOM | 725 | C | LEU | 73 | 148.400 | 81.544 | 109.826 |
| ATOM | 726 | O | LEU | 73 | 147.650 | 80.580 | 109.584 |
| ATOM | 727 | CB | LEU | 73 | 148.827 | 82.985 | 107.810 |
| ATOM | 728 | CG | LEU | 73 | 147.883 | 82.573 | 106.679 |
| ATOM | 729 | CD1 | LEU | 73 | 147.537 | 83.802 | 105.841 |
| ATOM | 730 | CD2 | LEU | 73 | 148.527 | 81.482 | 105.825 |
| ATOM | 731 | N | THR | 74 | 149.352 | 81.219 | 110.674 |
| ATOM | 732 | HN | THR | 74 | 149.319 | 80.317 | 110.933 |
| ATOM | 733 | CA | THR | 74 | 150.401 | 81.900 | 111.284 |
| ATOM | 734 | C | THR | 74 | 151.463 | 80.918 | 111.604 |
| ATOM | 735 | O | THR | 74 | 151.431 | 80.644 | 112.832 |
| ATOM | 736 | CB | THR | 74 | 150.691 | 83.386 | 110.992 |
| ATOM | 737 | OG1 | THR | 74 | 151.586 | 83.721 | 109.943 |
| ATOM | 738 | HOG1 | THR | 74 | 152.518 | 83.590 | 110.218 |
| ATOM | 739 | CG2 | THR | 74 | 150.935 | 84.192 | 112.269 |
| ATOM | 740 | N | PRO | 75 | 152.352 | 80.337 | 110.765 |
| ATOM | 741 | CA | PRO | 75 | 153.177 | 79.236 | 111.069 |
| ATOM | 742 | C | PRO | 75 | 153.942 | 79.230 | 112.342 |
| ATOM | 743 | O | PRO | 75 | 154.808 | 80.109 | 112.571 |
| ATOM | 744 | CB | PRO | 75 | 154.043 | 78.927 | 109.841 |
| ATOM | 745 | CG | PRO | 75 | 153.912 | 80.191 | 109.000 |
| ATOM | 746 | CD | PRO | 75 | 152.562 | 80.744 | 109.449 |
| ATOM | 747 | N | ASP | 76 | 153.777 | 78.332 | 113.308 |
| ATOM | 748 | HN | ASP | 76 | 154.317 | 78.422 | 114.072 |
| ATOM | 749 | CA | ASP | 76 | 152.879 | 77.264 | 113.298 |
| ATOM | 750 | C | ASP | 76 | 151.892 | 77.153 | 114.404 |
| ATOM | 751 | O | ASP | 76 | 152.226 | 77.243 | 115.615 |
| ATOM | 752 | CB | ASP | 76 | 153.632 | 75.954 | 113.016 |
| ATOM | 753 | CG | ASP | 76 | 152.785 | 75.113 | 112.176 |
| ATOM | 754 | OD1 | ASP | 76 | 152.210 | 74.123 | 112.674 |
| ATOM | 755 | OD2 | ASP | 76 | 152.636 | 75.398 | 110.967 |
| ATOM | 756 | N | CYS | 77 | 150.592 | 76.950 | 114.225 |
| ATOM | 757 | HN | CYS | 77 | 150.075 | 76.854 | 115.004 |
| ATOM | 758 | CA | CYS | 77 | 149.896 | 76.871 | 113.013 |
| ATOM | 759 | C | CYS | 77 | 149.130 | 78.089 | 112.682 |
| ATOM | 760 | O | CYS | 77 | 149.282 | 78.516 | 111.513 |
| ATOM | 761 | CB | CYS | 77 | 149.013 | 75.611 | 112.961 |
| ATOM | 762 | SG | CYS | 77 | 149.064 | 74.805 | 111.379 |
| ATOM | 763 | N | LYS | 78 | 148.334 | 78.707 | 113.555 |
| ATOM | 764 | HN | LYS | 78 | 148.257 | 78.358 | 114.423 |
| ATOM | 765 | CA | LYS | 78 | 147.578 | 79.851 | 113.363 |
| ATOM | 766 | C | LYS | 78 | 148.088 | 81.062 | 114.048 |
| ATOM | 767 | O | LYS | 78 | 147.870 | 82.112 | 113.403 |
| ATOM | 768 | CB | LYS | 78 | 146.083 | 79.531 | 113.572 |
| ATOM | 769 | CG | LYS | 78 | 145.105 | 80.415 | 112.775 |
| ATOM | 770 | CD | LYS | 78 | 145.103 | 80.116 | 111.269 |
| ATOM | 771 | CE | LYS | 78 | 144.036 | 80.927 | 110.528 |
| ATOM | 772 | NZ | LYS | 78 | 144.491 | 81.430 | 109.229 |
| ATOM | 773 | HNZ | LYS | 78 | 145.049 | 80.741 | 108.728 |
| ATOM | 774 | HNZ | LYS | 78 | 143.669 | 81.647 | 108.667 |
| ATOM | 775 | HNZ | LYS | 78 | 145.000 | 82.299 | 109.394 |
| ATOM | 776 | N | SER | 79 | 148.729 | 81.304 | 115.196 |

-31-

| ATOM | 777 | HN | SER | 79 | 148.836 | 82.226 | 115.344 |
| ATOM | 778 | CA | SER | 79 | 149.292 | 80.544 | 116.241 |
| ATOM | 779 | C | SER | 79 | 150.658 | 80.996 | 116.572 |
| ATOM | 780 | O | SER | 79 | 150.797 | 81.466 | 117.732 |
| ATOM | 781 | CB | SER | 79 | 149.158 | 79.022 | 116.458 |
| ATOM | 782 | OG | SER | 79 | 147.823 | 78.550 | 116.591 |
| ATOM | 783 | HOG | SER | 79 | 147.325 | 78.723 | 115.765 |
| ATOM | 784 | N | LEU | 80 | 151.668 | 80.922 | 115.703 |
| ATOM | 785 | CA | LEU | 80 | 152.963 | 81.431 | 115.833 |
| ATOM | 786 | C | LEU | 80 | 153.247 | 82.594 | 114.957 |
| ATOM | 787 | O | LEU | 80 | 152.762 | 83.663 | 115.416 |
| ATOM | 788 | CB | LEU | 80 | 153.999 | 80.296 | 115.934 |
| ATOM | 789 | CG | LEU | 80 | 155.297 | 80.733 | 116.619 |
| ATOM | 790 | CD1 | LEU | 80 | 155.485 | 79.940 | 117.913 |
| ATOM | 791 | CD2 | LEU | 80 | 156.484 | 80.469 | 115.689 |
| ATOM | 792 | N | TRP | 81 | 153.935 | 82.560 | 113.803 |
| ATOM | 793 | HN | TRP | 81 | 154.226 | 81.723 | 113.492 |
| ATOM | 794 | CA | TRP | 81 | 154.290 | 83.629 | 112.961 |
| ATOM | 795 | C | TRP | 81 | 154.985 | 83.254 | 111.709 |
| ATOM | 796 | O | TRP | 81 | 154.324 | 83.406 | 110.650 |
| ATOM | 797 | CB | TRP | 81 | 154.962 | 84.854 | 113.625 |
| ATOM | 798 | CG | TRP | 81 | 154.110 | 86.054 | 113.634 |
| ATOM | 799 | CD1 | TRP | 81 | 153.770 | 86.758 | 114.792 |
| ATOM | 800 | CD2 | TRP | 81 | 153.492 | 86.724 | 112.578 |
| ATOM | 801 | NE1 | TRP | 81 | 152.996 | 87.772 | 114.453 |
| ATOM | 802 | HNE1 | TRP | 81 | 152.634 | 88.391 | 115.059 |
| ATOM | 803 | CE2 | TRP | 81 | 152.799 | 87.796 | 113.157 |
| ATOM | 804 | CE3 | TRP | 81 | 153.466 | 86.500 | 111.179 |
| ATOM | 805 | CZ2 | TRP | 81 | 152.039 | 88.700 | 112.378 |
| ATOM | 806 | CZ3 | TRP | 81 | 152.687 | 87.383 | 110.391 |
| ATOM | 807 | CH2 | TRP | 81 | 151.989 | 88.471 | 110.979 |
| ATOM | 808 | N | ASN | 82 | 156.237 | 82.793 | 111.687 |
| ATOM | 809 | HN | ASN | 82 | 156.556 | 82.385 | 112.473 |
| ATOM | 810 | CA | ASN | 82 | 157.126 | 82.884 | 110.614 |
| ATOM | 811 | C | ASN | 82 | 157.270 | 81.778 | 109.638 |
| ATOM | 812 | O | ASN | 82 | 157.334 | 80.570 | 110.006 |
| ATOM | 813 | CB | ASN | 82 | 158.455 | 83.363 | 111.227 |
| ATOM | 814 | CG | ASN | 82 | 159.240 | 84.228 | 110.346 |
| ATOM | 815 | OD1 | ASN | 82 | 160.047 | 83.703 | 109.548 |
| ATOM | 816 | ND2 | ASN | 82 | 159.123 | 85.532 | 110.380 |
| ATOM | 817 | HND2 | ASN | 82 | 159.677 | 86.063 | 109.838 |
| ATOM | 818 | HND2 | ASN | 82 | 158.489 | 85.940 | 110.941 |
| ATOM | 819 | N | GLY | 83 | 157.333 | 82.163 | 108.368 |
| ATOM | 820 | HN | GLY | 83 | 157.189 | 83.081 | 108.229 |
| ATOM | 821 | CA | GLY | 83 | 157.593 | 81.402 | 107.223 |
| ATOM | 822 | C | GLY | 83 | 157.453 | 82.153 | 105.965 |
| ATOM | 823 | O | GLY | 83 | 156.517 | 81.783 | 105.215 |
| ATOM | 824 | N | ASP | 84 | 158.292 | 83.151 | 105.690 |
| ATOM | 825 | HN | ASP | 84 | 158.966 | 83.290 | 106.330 |
| ATOM | 826 | CA | ASP | 84 | 158.327 | 84.030 | 104.599 |
| ATOM | 827 | C | ASP | 84 | 157.071 | 84.644 | 104.065 |
| ATOM | 828 | O | ASP | 84 | 156.934 | 84.881 | 102.842 |
| ATOM | 829 | CB | ASP | 84 | 159.460 | 83.592 | 103.633 |
| ATOM | 830 | CG | ASP | 84 | 159.065 | 82.772 | 102.480 |
| ATOM | 831 | OD1 | ASP | 84 | 158.775 | 81.563 | 102.610 |
| ATOM | 832 | OD2 | ASP | 84 | 159.000 | 83.272 | 101.332 |
| ATOM | 833 | N | THR | 85 | 155.968 | 85.038 | 104.691 |
| ATOM | 834 | HN | THR | 85 | 155.241 | 85.195 | 104.116 |
| ATOM | 835 | CA | THR | 85 | 155.688 | 85.277 | 106.038 |
| ATOM | 836 | C | THR | 85 | 156.732 | 85.670 | 107.005 |

| ATOM | 837 | O    | THR | 85 | 156.919 | 84.955 | 108.026 |
|------|-----|------|-----|----|---------|--------|---------|
| ATOM | 838 | CB   | THR | 85 | 154.321 | 84.728 | 106.495 |
| ATOM | 839 | OG1  | THR | 85 | 153.584 | 85.638 | 107.295 |
| ATOM | 840 | HOG1 | THR | 85 | 152.657 | 85.503 | 107.007 |
| ATOM | 841 | CG2  | THR | 85 | 154.257 | 83.338 | 107.135 |
| ATOM | 842 | N    | GLY | 86 | 157.413 | 86.782 | 106.731 |
| ATOM | 843 | HN   | GLY | 86 | 157.232 | 87.193 | 105.906 |
| ATOM | 844 | CA   | GLY | 86 | 158.352 | 87.401 | 107.565 |
| ATOM | 845 | C    | GLY | 86 | 157.747 | 88.498 | 108.336 |
| ATOM | 846 | O    | GLY | 86 | 158.299 | 89.617 | 108.225 |
| ATOM | 847 | N    | GLU | 87 | 156.669 | 88.255 | 109.081 |
| ATOM | 848 | HN   | GLU | 87 | 156.510 | 87.344 | 109.245 |
| ATOM | 849 | CA   | GLU | 87 | 155.740 | 89.152 | 109.626 |
| ATOM | 850 | C    | GLU | 87 | 155.027 | 89.915 | 108.574 |
| ATOM | 851 | O    | GLU | 87 | 155.381 | 91.084 | 108.741 |
| ATOM | 852 | CB   | GLU | 87 | 156.205 | 89.875 | 110.909 |
| ATOM | 853 | CG   | GLU | 87 | 156.184 | 88.984 | 112.169 |
| ATOM | 854 | CD   | GLU | 87 | 157.244 | 87.969 | 112.233 |
| ATOM | 855 | OE1  | GLU | 87 | 158.410 | 88.288 | 112.548 |
| ATOM | 856 | OE2  | GLU | 87 | 157.011 | 86.765 | 111.877 |
| ATOM | 857 | N    | CYS | 88 | 154.009 | 89.267 | 108.005 |
| ATOM | 858 | HN   | CYS | 88 | 153.741 | 88.467 | 108.420 |
| ATOM | 859 | CA   | CYS | 88 | 153.301 | 89.623 | 106.558 |
| ATOM | 860 | C    | CYS | 88 | 153.989 | 89.205 | 105.618 |
| ATOM | 861 | O    | CYS | 88 | 154.073 | 87.983 | 105.292 |
| ATOM | 862 | CB   | CYS | 88 | 151.854 | 89.101 | 106.933 |
| ATOM | 863 | SG   | CYS | 88 | 150.624 | 90.247 | 106.269 |
| ATOM | 864 | N    | THR | 89 | 154.496 | 90.187 | 104.876 |
| ATOM | 865 | HN   | THR | 89 | 154.350 | 91.058 | 105.196 |
| ATOM | 866 | CA   | THR | 89 | 155.214 | 90.104 | 103.666 |
| ATOM | 867 | C    | THR | 89 | 154.446 | 90.143 | 102.397 |
| ATOM | 868 | O    | THR | 89 | 155.036 | 90.711 | 101.431 |
| ATOM | 869 | CB   | THR | 89 | 156.604 | 89.413 | 103.603 |
| ATOM | 870 | OG1  | THR | 89 | 156.679 | 88.129 | 104.203 |
| ATOM | 871 | HOG1 | THR | 89 | 155.801 | 87.995 | 104.616 |
| ATOM | 872 | CG2  | THR | 89 | 157.715 | 90.301 | 104.177 |
| ATOM | 873 | N    | ASP | 90 | 153.208 | 89.634 | 102.253 |
| ATOM | 874 | HN   | ASP | 90 | 152.869 | 89.166 | 102.993 |
| ATOM | 875 | CA   | ASP | 90 | 152.377 | 89.739 | 101.120 |
| ATOM | 876 | C    | ASP | 90 | 152.208 | 91.108 | 100.589 |
| ATOM | 877 | O    | ASP | 90 | 152.789 | 91.327 | 99.489  |
| ATOM | 878 | CB   | ASP | 90 | 151.100 | 88.866 | 101.133 |
| ATOM | 879 | CG   | ASP | 90 | 150.519 | 88.478 | 99.830  |
| ATOM | 880 | OD1  | ASP | 90 | 149.629 | 87.593 | 99.796  |
| ATOM | 881 | OD2  | ASP | 90 | 150.856 | 88.973 | 98.725  |
| ATOM | 882 | N    | ASN | 91 | 151.512 | 92.063 | 101.220 |
| ATOM | 883 | HN   | ASN | 91 | 151.051 | 91.792 | 101.992 |
| ATOM | 884 | CA   | ASN | 91 | 151.401 | 93.430 | 100.874 |
| ATOM | 885 | C    | ASN | 91 | 150.555 | 93.783 | 99.706  |
| ATOM | 886 | O    | ASN | 91 | 149.669 | 94.659 | 99.892  |
| ATOM | 887 | CB   | ASN | 91 | 152.754 | 94.193 | 100.912 |
| ATOM | 888 | CG   | ASN | 91 | 153.345 | 94.302 | 102.252 |
| ATOM | 889 | OD1  | ASN | 91 | 153.205 | 95.369 | 102.889 |
| ATOM | 890 | ND2  | ASN | 91 | 154.009 | 93.310 | 102.800 |
| ATOM | 891 | HND2 | ASN | 91 | 154.181 | 93.321 | 103.723 |
| ATOM | 892 | HND2 | ASN | 91 | 154.307 | 92.578 | 102.293 |
| ATOM | 893 | N    | ALA | 92 | 150.759 | 93.176 | 98.534  |
| ATOM | 894 | HN   | ALA | 92 | 151.471 | 92.570 | 98.601  |
| ATOM | 895 | CA   | ALA | 92 | 150.103 | 93.281 | 97.295  |
| ATOM | 896 | C    | ALA | 92 | 149.921 | 94.579 | 96.593  |

| | | | | | | | |
|---|---|---|---|---|---|---|---|
| ATOM | 897 | O | ALA | 92 | 150.325 | 94.645 | 95.403 |
| ATOM | 898 | CB | ALA | 92 | 148.849 | 92.387 | 97.308 |
| ATOM | 899 | N | TYR | 93 | 149.348 | 95.601 | 97.224 |
| ATOM | 900 | HN | TYR | 93 | 149.366 | 95.451 | 98.150 |
| ATOM | 901 | CA | TYR | 93 | 148.741 | 96.785 | 96.772 |
| ATOM | 902 | C | TYR | 93 | 149.462 | 97.756 | 95.920 |
| ATOM | 903 | O | TYR | 93 | 149.765 | 97.489 | 94.723 |
| ATOM | 904 | CB | TYR | 93 | 147.264 | 96.603 | 96.350 |
| ATOM | 905 | CG | TYR | 93 | 146.370 | 95.969 | 97.328 |
| ATOM | 906 | CD1 | TYR | 93 | 145.733 | 94.761 | 96.949 |
| ATOM | 907 | CD2 | TYR | 93 | 146.148 | 96.547 | 98.606 |
| ATOM | 908 | CE1 | TYR | 93 | 144.845 | 94.130 | 97.848 |
| ATOM | 909 | CE2 | TYR | 93 | 145.262 | 95.915 | 99.509 |
| ATOM | 910 | CZ | TYR | 93 | 144.614 | 94.721 | 99.112 |
| ATOM | 911 | OH | TYR | 93 | 143.747 | 94.130 | 99.959 |
| ATOM | 912 | HOH | TYR | 93 | 143.565 | 94.525 | 100.837 |
| ATOM | 913 | N | ILE | 94 | 149.756 | 98.919 | 96.482 |
| ATOM | 914 | HN | ILE | 94 | 149.402 | 99.092 | 97.335 |
| ATOM | 915 | CA | ILE | 94 | 150.534 | 99.957 | 95.948 |
| ATOM | 916 | C | ILE | 94 | 149.917 | 101.262 | 96.248 |
| ATOM | 917 | O | ILE | 94 | 150.194 | 101.883 | 97.314 |
| ATOM | 918 | CB | ILE | 94 | 152.085 | 99.896 | 96.085 |
| ATOM | 919 | CG1 | ILE | 94 | 152.748 | 98.993 | 95.032 |
| ATOM | 920 | CG2 | ILE | 94 | 152.668 | 99.576 | 97.476 |
| ATOM | 921 | CD1 | ILE | 94 | 153.137 | 99.769 | 93.767 |
| ATOM | 922 | N | ASP | 95 | 149.066 | 101.712 | 95.332 |
| ATOM | 923 | HN | ASP | 95 | 148.995 | 101.217 | 94.537 |
| ATOM | 924 | CA | ASP | 95 | 148.265 | 102.846 | 95.441 |
| ATOM | 925 | C | ASP | 95 | 146.824 | 102.536 | 95.321 |
| ATOM | 926 | O | ASP | 95 | 146.172 | 102.507 | 96.400 |
| ATOM | 927 | CB | ASP | 95 | 148.825 | 103.952 | 94.526 |
| ATOM | 928 | CG | ASP | 95 | 148.113 | 105.218 | 94.678 |
| ATOM | 929 | OD1 | ASP | 95 | 147.244 | 105.528 | 93.840 |
| ATOM | 930 | OD2 | ASP | 95 | 148.363 | 105.986 | 95.629 |
| ATOM | 931 | N | ILE | 96 | 146.248 | 102.299 | 94.143 |
| ATOM | 932 | CA | ILE | 96 | 144.898 | 102.039 | 93.908 |
| ATOM | 933 | C | ILE | 96 | 144.226 | 103.067 | 93.065 |
| ATOM | 934 | O | ILE | 96 | 143.980 | 102.868 | 91.850 |
| ATOM | 935 | CB | ILE | 96 | 144.612 | 100.523 | 93.754 |
| ATOM | 936 | CG1 | ILE | 96 | 145.057 | 99.868 | 92.434 |
| ATOM | 937 | CG2 | ILE | 96 | 143.159 | 100.158 | 94.090 |
| ATOM | 938 | CD1 | ILE | 96 | 146.334 | 99.039 | 92.623 |
| ATOM | 939 | N | GLN | 97 | 143.829 | 104.258 | 93.505 |
| ATOM | 940 | HN | GLN | 97 | 143.387 | 104.809 | 92.885 |
| ATOM | 941 | CA | GLN | 97 | 143.998 | 104.780 | 94.790 |
| ATOM | 942 | C | GLN | 97 | 143.014 | 104.307 | 95.786 |
| ATOM | 943 | O | GLN | 97 | 141.790 | 104.611 | 95.697 |
| ATOM | 944 | CB | GLN | 97 | 144.161 | 106.313 | 94.726 |
| ATOM | 945 | CG | GLN | 97 | 144.815 | 106.875 | 96.003 |
| ATOM | 946 | CD | GLN | 97 | 145.375 | 108.223 | 95.870 |
| ATOM | 947 | OE1 | GLN | 97 | 144.640 | 109.236 | 95.947 |
| ATOM | 948 | NE2 | GLN | 97 | 146.662 | 108.375 | 95.675 |
| ATOM | 949 | HNE2 | GLN | 97 | 147.035 | 109.234 | 95.596 |
| ATOM | 950 | HNE2 | GLN | 97 | 147.208 | 107.614 | 95.617 |
| ATOM | 951 | N | LEU | 98 | 143.516 | 103.555 | 96.759 |
| ATOM | 952 | HN | LEU | 98 | 144.402 | 103.266 | 96.640 |
| ATOM | 953 | CA | LEU | 98 | 142.909 | 103.129 | 97.944 |
| ATOM | 954 | C | LEU | 98 | 142.159 | 101.854 | 97.878 |
| ATOM | 955 | O | LEU | 98 | 141.190 | 101.697 | 97.099 |
| ATOM | 956 | CB | LEU | 98 | 142.286 | 104.211 | 98.851 |

| ATOM | 957 | CG | LEU | 98 | 143.338 | 104.851 | 99.766 |
| ATOM | 958 | CD1 | LEU | 98 | 143.135 | 106.367 | 99.802 |
| ATOM | 959 | CD2 | LEU | 98 | 143.224 | 104.290 | 101.186 |
| ATOM | 960 | N | ARG | 99 | 142.443 | 100.793 | 98.623 |
| ATOM | 961 | HN | ARG | 99 | 141.935 | 100.017 | 98.465 |
| ATOM | 962 | CA | ARG | 99 | 143.420 | 100.718 | 99.624 |
| ATOM | 963 | C | ARG | 99 | 144.819 | 100.550 | 99.185 |
| ATOM | 964 | O | ARG | 99 | 145.141 | 99.620 | 98.398 |
| ATOM | 965 | CB | ARG | 99 | 143.003 | 99.861 | 100.839 |
| ATOM | 966 | CG | ARG | 99 | 142.869 | 98.341 | 100.628 |
| ATOM | 967 | CD | ARG | 99 | 141.410 | 97.867 | 100.691 |
| ATOM | 968 | NE | ARG | 99 | 140.989 | 97.709 | 102.013 |
| ATOM | 969 | HNE | ARG | 99 | 141.653 | 97.644 | 102.674 |
| ATOM | 970 | CZ | ARG | 99 | 139.772 | 97.636 | 102.530 |
| ATOM | 971 | NH1 | ARG | 99 | 139.803 | 97.517 | 103.830 |
| ATOM | 972 | HNH1 | ARG | 99 | 139.026 | 97.442 | 104.351 |
| ATOM | 973 | HNH1 | ARG | 99 | 140.663 | 97.510 | 104.204 |
| ATOM | 974 | NH2 | ARG | 99 | 138.600 | 97.673 | 101.923 |
| ATOM | 975 | HNH2 | ARG | 99 | 137.807 | 97.616 | 102.426 |
| ATOM | 976 | HNH2 | ARG | 99 | 138.557 | 97.753 | 100.987 |
| ATOM | 977 | N | ILE | 100 | 145.682 | 101.433 | 99.675 |
| ATOM | 978 | HN | ILE | 100 | 145.314 | 102.111 | 100.212 |
| ATOM | 979 | CA | ILE | 100 | 147.072 | 101.483 | 99.498 |
| ATOM | 980 | C | ILE | 100 | 147.792 | 100.222 | 99.817 |
| ATOM | 981 | O | ILE | 100 | 148.526 | 99.739 | 98.920 |
| ATOM | 982 | CB | ILE | 100 | 147.570 | 102.841 | 100.071 |
| ATOM | 983 | CG1 | ILE | 100 | 147.944 | 103.824 | 98.952 |
| ATOM | 984 | CG2 | ILE | 100 | 148.696 | 102.853 | 101.124 |
| ATOM | 985 | CD1 | ILE | 100 | 146.881 | 104.912 | 98.756 |
| ATOM | 986 | N | ALA | 101 | 147.661 | 99.627 | 101.003 |
| ATOM | 987 | HN | ALA | 101 | 147.091 | 100.056 | 101.614 |
| ATOM | 988 | CA | ALA | 101 | 148.270 | 98.441 | 101.434 |
| ATOM | 989 | C | ALA | 101 | 147.547 | 97.789 | 102.547 |
| ATOM | 990 | O | ALA | 101 | 147.144 | 96.617 | 102.376 |
| ATOM | 991 | CB | ALA | 101 | 149.777 | 98.582 | 101.740 |
| ATOM | 992 | N | SER | 102 | 147.265 | 98.299 | 103.740 |
| ATOM | 993 | HN | SER | 102 | 147.120 | 97.697 | 104.445 |
| ATOM | 994 | CA | SER | 102 | 147.160 | 99.656 | 104.067 |
| ATOM | 995 | C | SER | 102 | 145.802 | 100.170 | 103.755 |
| ATOM | 996 | O | SER | 102 | 145.736 | 101.035 | 102.849 |
| ATOM | 997 | CB | SER | 102 | 147.655 | 100.097 | 105.466 |
| ATOM | 998 | OG | SER | 102 | 148.444 | 99.184 | 106.224 |
| ATOM | 999 | HOG | SER | 102 | 148.024 | 98.299 | 106.179 |
| ATOM | 1000 | N | PHE | 103 | 144.645 | 99.813 | 104.321 |
| ATOM | 1001 | HN | PHE | 103 | 143.868 | 100.265 | 104.043 |
| ATOM | 1002 | CA | PHE | 103 | 144.500 | 98.816 | 105.291 |
| ATOM | 1003 | C | PHE | 103 | 143.856 | 97.568 | 104.840 |
| ATOM | 1004 | O | PHE | 103 | 142.701 | 97.585 | 104.324 |
| ATOM | 1005 | CB | PHE | 103 | 143.928 | 99.360 | 106.615 |
| ATOM | 1006 | CG | PHE | 103 | 144.623 | 98.770 | 107.764 |
| ATOM | 1007 | CD1 | PHE | 103 | 145.691 | 99.485 | 108.365 |
| ATOM | 1008 | CD2 | PHE | 103 | 144.236 | 97.498 | 108.267 |
| ATOM | 1009 | CE1 | PHE | 103 | 146.399 | 98.915 | 109.450 |
| ATOM | 1010 | CE2 | PHE | 103 | 144.943 | 96.924 | 109.351 |
| ATOM | 1011 | CZ | PHE | 103 | 146.021 | 97.637 | 109.931 |
| ATOM | 1012 | N | SER | 104 | 144.549 | 96.448 | 105.009 |
| ATOM | 1013 | HN | SER | 104 | 145.426 | 96.529 | 105.340 |
| ATOM | 1014 | CA | SER | 104 | 144.122 | 95.141 | 104.755 |
| ATOM | 1015 | C | SER | 104 | 144.594 | 94.151 | 105.745 |
| ATOM | 1016 | O | SER | 104 | 143.674 | 93.550 | 106.351 |

| ATOM | 1017 | CB   | SER | 104 | 144.242 | 94.709 | 103.282 |
|------|------|------|-----|-----|---------|--------|---------|
| ATOM | 1018 | OG   | SER | 104 | 143.171 | 95.296 | 102.556 |
| ATOM | 1019 | HOG  | SER | 104 | 142.941 | 96.103 | 103.062 |
| ATOM | 1020 | N    | GLN | 105 | 145.837 | 93.800 | 106.090 |
| ATOM | 1021 | HN   | GLN | 105 | 145.895 | 93.152 | 106.766 |
| ATOM | 1022 | CA   | GLN | 105 | 147.094 | 94.214 | 105.613 |
| ATOM | 1023 | C    | GLN | 105 | 147.734 | 95.447 | 106.130 |
| ATOM | 1024 | O    | GLN | 105 | 147.189 | 96.579 | 106.014 |
| ATOM | 1025 | CB   | GLN | 105 | 147.418 | 93.961 | 104.123 |
| ATOM | 1026 | CG   | GLN | 105 | 147.266 | 92.511 | 103.622 |
| ATOM | 1027 | CD   | GLN | 105 | 147.426 | 92.297 | 102.176 |
| ATOM | 1028 | OE1  | GLN | 105 | 146.975 | 93.077 | 101.302 |
| ATOM | 1029 | NE2  | GLN | 105 | 148.065 | 91.232 | 101.764 |
| ATOM | 1030 | HNE2 | GLN | 105 | 148.258 | 91.122 | 100.851 |
| ATOM | 1031 | HNE2 | GLN | 105 | 148.326 | 90.576 | 102.385 |
| ATOM | 1032 | N    | ASN | 106 | 148.915 | 95.283 | 106.708 |
| ATOM | 1033 | HN   | ASN | 106 | 149.083 | 94.431 | 107.067 |
| ATOM | 1034 | CA   | ASN | 106 | 149.953 | 96.206 | 106.849 |
| ATOM | 1035 | C    | ASN | 106 | 150.978 | 96.087 | 105.777 |
| ATOM | 1036 | O    | ASN | 106 | 151.210 | 97.149 | 105.153 |
| ATOM | 1037 | CB   | ASN | 106 | 150.581 | 96.139 | 108.253 |
| ATOM | 1038 | CG   | ASN | 106 | 149.859 | 96.820 | 109.329 |
| ATOM | 1039 | OD1  | ASN | 106 | 149.881 | 98.068 | 109.424 |
| ATOM | 1040 | ND2  | ASN | 106 | 149.192 | 96.109 | 110.202 |
| ATOM | 1041 | HND2 | ASN | 106 | 148.711 | 96.531 | 110.889 |
| ATOM | 1042 | HND2 | ASN | 106 | 149.204 | 95.171 | 110.138 |
| ATOM | 1043 | N    | CYS | 107 | 151.686 | 95.024 | 105.371 |
| ATOM | 1044 | HN   | CYS | 107 | 152.252 | 95.157 | 104.633 |
| ATOM | 1045 | CA   | CYS | 107 | 151.657 | 93.734 | 105.912 |
| ATOM | 1046 | C    | CYS | 107 | 152.925 | 93.171 | 106.457 |
| ATOM | 1047 | O    | CYS | 107 | 153.917 | 92.916 | 105.722 |
| ATOM | 1048 | CB   | CYS | 107 | 150.887 | 92.885 | 104.872 |
| ATOM | 1049 | SG   | CYS | 107 | 151.233 | 91.155 | 104.681 |
| ATOM | 1050 | N    | ASP | 108 | 153.149 | 92.867 | 107.732 |
| ATOM | 1051 | HN   | ASP | 108 | 153.907 | 92.337 | 107.894 |
| ATOM | 1052 | CA   | ASP | 108 | 152.423 | 93.222 | 108.872 |
| ATOM | 1053 | C    | ASP | 108 | 153.368 | 93.438 | 110.005 |
| ATOM | 1054 | O    | ASP | 108 | 153.744 | 92.498 | 110.758 |
| ATOM | 1055 | CB   | ASP | 108 | 151.290 | 92.211 | 109.165 |
| ATOM | 1056 | CG   | ASP | 108 | 149.939 | 92.758 | 109.033 |
| ATOM | 1057 | OD1  | ASP | 108 | 149.319 | 93.200 | 110.023 |
| ATOM | 1058 | OD2  | ASP | 108 | 149.381 | 92.790 | 107.923 |
| ATOM | 1059 | N    | ILE | 109 | 153.912 | 94.601 | 110.341 |
| ATOM | 1060 | HN   | ILE | 109 | 154.497 | 94.585 | 111.076 |
| ATOM | 1061 | CA   | ILE | 109 | 153.720 | 95.851 | 109.727 |
| ATOM | 1062 | C    | ILE | 109 | 154.399 | 96.036 | 108.429 |
| ATOM | 1063 | O    | ILE | 109 | 153.757 | 96.519 | 107.470 |
| ATOM | 1064 | CB   | ILE | 109 | 153.887 | 97.105 | 110.629 |
| ATOM | 1065 | CG1  | ILE | 109 | 155.198 | 97.234 | 111.428 |
| ATOM | 1066 | CG2  | ILE | 109 | 152.681 | 97.347 | 111.549 |
| ATOM | 1067 | CD1  | ILE | 109 | 156.158 | 98.237 | 110.776 |
| ATOM | 1068 | OXT  | GLN | 109 | 155.598 | 95.737 | 108.216 |

| CONECT | 1 | 5 | 2 | 3 | 4 |
|--------|---|---|---|---|---|
| CONECT | 2 | 1 |   |   |   |
| CONECT | 3 | 1 |   |   |   |
| CONECT | 4 | 1 |   |   |   |
| CONECT | 5 | 1 | 6 | 8 |   |
| CONECT | 6 | 7 | 5 | 10 |  |
| CONECT | 7 | 6 |   |   |   |
| CONECT | 8 | 9 | 5 |   |   |

-36-

```
CONECT      9     8    30
CONECT     10    12     6    11
CONECT     11    10
CONECT     12    10    13    15
CONECT     13    12    14    19
CONECT     14    13
CONECT     15    16    12
CONECT     16    15    17    18
CONECT     17    16
CONECT     18    16
CONECT     19    20    21    13
CONECT     20    19
CONECT     21    19    22
CONECT     22    21    23    24
CONECT     23    22
CONECT     24    26    22    25
CONECT     25    24
CONECT     26    24    27    29
CONECT     27    28    26    31
CONECT     28    27
CONECT     29    30    26
CONECT     30    29     9
CONECT     31    32    27
CONECT     32    31    33    35
CONECT     33    34    32    38
CONECT     34    33
CONECT     35    36    37    32
CONECT     36    35
CONECT     37    35
CONECT     38    33    40    39
CONECT     39    38
CONECT     40    38    41    43
CONECT     41    42    40    50
CONECT     42    41
CONECT     43    44    40
CONECT     44    43    45    47
CONECT     45    44    48    46
CONECT     46    45
CONECT     47    44    49
CONECT     48    45    49
CONECT     49    47    48
CONECT     50    51    41    56
CONECT     51    50    52    54
CONECT     52    53    51    57
CONECT     53    52
CONECT     54    55    51
CONECT     55    54    56
CONECT     56    55    50
CONECT     57    52    59    58
CONECT     58    57
CONECT     59    57    60    62
CONECT     60    61    59    66
CONECT     61    60
CONECT     62    63    64    59
CONECT     63    62    65
CONECT     64    62
CONECT     65    63
CONECT     66    60    68    67
CONECT     67    66
CONECT     68    66    69    71
```

-37-

```
CONECT   69   70   68   74
CONECT   70   69
CONECT   71   72   68
CONECT   72   71   73
CONECT   73   72
CONECT   74   69   76   75
CONECT   75   74
CONECT   76   74   77   79
CONECT   77   78   76   83
CONECT   78   77
CONECT   79   80   82   76
CONECT   80   79   81
CONECT   81   80
CONECT   82   79
CONECT   83   77   85   84
CONECT   84   83
CONECT   85   83   86   88
CONECT   86   87   85   95
CONECT   87   86
CONECT   88   89   85
CONECT   89   88   90
CONECT   90   89   91   92
CONECT   91   90
CONECT   92   90   93   94
CONECT   93   92
CONECT   94   92
CONECT   95   86   97   96
CONECT   96   95
CONECT   97   95   98  100
CONECT   98   99   97  103
CONECT   99   98
CONECT  100  101   97
CONECT  101  100  102
CONECT  102  101
CONECT  103   98  104  109
CONECT  104  103  105  107
CONECT  105  106  104  110
CONECT  106  105
CONECT  107  108  104
CONECT  108  107  109
CONECT  109  108  103
CONECT  110  105  112  111
CONECT  111  110
CONECT  112  110  113  115
CONECT  113  114  112  119
CONECT  114  113
CONECT  115  116  112
CONECT  116  115  117  118
CONECT  117  116
CONECT  118  116
CONECT  119  113  121  120
CONECT  120  119
CONECT  121  124  119  122
CONECT  122  123  121  128
CONECT  123  122
CONECT  124  121  125
CONECT  125  124  126  127
CONECT  126  125
CONECT  127  125
CONECT  128  122  130  129
```

```
CONECT  129  128
CONECT  130  128  131  133
CONECT  131  132  130  138
CONECT  132  131
CONECT  133  134  130
CONECT  134  133  135
CONECT  135  134  136  137
CONECT  136  135
CONECT  137  135
CONECT  138  131  139  144
CONECT  139  138  140  142
CONECT  140  141  139  145
CONECT  141  140
CONECT  142  143  139
CONECT  143  142  144
CONECT  144  143  138
CONECT  145  140  147  146
CONECT  146  145
CONECT  147  145  148  150
CONECT  148  149  147  154
CONECT  149  148
CONECT  150  151  152  147
CONECT  151  150  153
CONECT  152  150
CONECT  153  151
CONECT  154  148  156  155
CONECT  155  154
CONECT  156  159  154  157
CONECT  157  158  156  163
CONECT  158  157
CONECT  159  156  160
CONECT  160  159  161  162
CONECT  161  160
CONECT  162  160
CONECT  163  157  165  164
CONECT  164  163
CONECT  165  163  166  168
CONECT  166  167  165  180
CONECT  167  166
CONECT  168  169  165
CONECT  169  168  170
CONECT  170  169  171
CONECT  171  170  173  172
CONECT  172  171
CONECT  173  171  174  177
CONECT  174  173  175  176
CONECT  175  174
CONECT  176  174
CONECT  177  173  178  179
CONECT  178  177
CONECT  179  177
CONECT  180  166  182  181
CONECT  181  180
CONECT  182  180  183  185
CONECT  183  184  182  192
CONECT  184  183
CONECT  185  186  182
CONECT  186  185  187  189
CONECT  187  186  190  188
CONECT  188  187
```

```
CONECT   189   186   191
CONECT   190   187   191
CONECT   191   189   190
CONECT   192   183   194   193
CONECT   193   192
CONECT   194   192   195
CONECT   195   196   194   197
CONECT   196   195
CONECT   197   195   199   198
CONECT   198   197
CONECT   199   197   200   202
CONECT   200   201   199   206
CONECT   201   200
CONECT   202   203   204   199
CONECT   203   202   205
CONECT   204   202
CONECT   205   203
CONECT   206   200   208   207
CONECT   207   206
CONECT   208   206   209   211
CONECT   209   210   208   218
CONECT   210   209
CONECT   211   212   208
CONECT   212   211   213
CONECT   213   212   214   215
CONECT   214   213
CONECT   215   213   216   217
CONECT   216   215
CONECT   217   215
CONECT   218   209   220   219
CONECT   219   218
CONECT   220   218   221   223
CONECT   221   222   220   232
CONECT   222   221
CONECT   223   224   220
CONECT   224   223   225   226
CONECT   225   224   227
CONECT   226   224   228
CONECT   227   225   229
CONECT   228   226   229
CONECT   229   227   228   230
CONECT   230   229   231
CONECT   231   230
CONECT   232   221   234   233
CONECT   233   232
CONECT   234   232   235   237
CONECT   235   236   234   244
CONECT   236   235
CONECT   237   238   234
CONECT   238   237   239   240
CONECT   239   238   241
CONECT   240   238   242
CONECT   241   239   243
CONECT   242   240   243
CONECT   243   241   242
CONECT   244   235   246   245
CONECT   245   244
CONECT   246   249   244   247
CONECT   247   248   246   255
CONECT   248   247
```

```
CONECT  249  246  250
CONECT  250  249  251  252
CONECT  251  250
CONECT  252  250  254  253
CONECT  253  252
CONECT  254  252
CONECT  255  247  257  256
CONECT  256  255
CONECT  257  255  258  260
CONECT  258  259  257  266
CONECT  259  258
CONECT  260  261  257
CONECT  261  260  262  263
CONECT  262  261
CONECT  263  261  264  265
CONECT  264  263
CONECT  265  263
CONECT  266  258  268  267
CONECT  267  266
CONECT  268  266  269  271
CONECT  269  270  268  277
CONECT  270  269
CONECT  271  272  268
CONECT  272  271  273  274
CONECT  273  272
CONECT  274  272  275  276
CONECT  275  274
CONECT  276  274
CONECT  277  269  279  278
CONECT  278  277
CONECT  279  277  280  282
CONECT  280  281  279  286
CONECT  281  280
CONECT  282  283  285  279
CONECT  283  282  284
CONECT  284  283
CONECT  285  282
CONECT  286  280  288  287
CONECT  287  286
CONECT  288  286  289  291
CONECT  289  290  288  298
CONECT  290  289
CONECT  291  292  288
CONECT  292  291  293
CONECT  293  292  294  295
CONECT  294  293
CONECT  295  293  296  297
CONECT  296  295
CONECT  297  295
CONECT  298  289  300  299
CONECT  299  298
CONECT  300  298  301  303
CONECT  301  302  300  310
CONECT  302  301
CONECT  303  304  300
CONECT  304  303  305  307
CONECT  305  304  308  306
CONECT  306  305
CONECT  307  304  309
CONECT  308  305  309
```

```
CONECT   309   307   308
CONECT   310   301   312   311
CONECT   311   310
CONECT   312   310   313   315
CONECT   313   314   312   318
CONECT   314   313
CONECT   315   316   312
CONECT   316   315   317
CONECT   317   316
CONECT   318   313   320   319
CONECT   319   318
CONECT   320   318   321   323
CONECT   321   322   320   326
CONECT   322   321
CONECT   323   324   320
CONECT   324   323   325
CONECT   325   324
CONECT   326   321   328   327
CONECT   327   326
CONECT   328   326   329   331
CONECT   329   330   328   340
CONECT   330   329
CONECT   331   332   328
CONECT   332   331   333   334
CONECT   333   332   335
CONECT   334   332   336
CONECT   335   333   337
CONECT   336   334   337
CONECT   337   335   336   338
CONECT   338   337   339
CONECT   339   338
CONECT   340   329   342   341
CONECT   341   340
CONECT   342   340   343   345
CONECT   343   344   342   352
CONECT   344   343
CONECT   345   346   342
CONECT   346   345   347   348
CONECT   347   346   349
CONECT   348   346   350
CONECT   349   347   351
CONECT   350   348   351
CONECT   351   349   350
CONECT   352   343   354   353
CONECT   353   352
CONECT   354   352   355   357
CONECT   355   356   354   361
CONECT   356   355
CONECT   357   358   354
CONECT   358   357   359
CONECT   359   358   360
CONECT   360   359
CONECT   361   355   363   362
CONECT   362   361
CONECT   363   361   364   366
CONECT   364   365   363   370
CONECT   365   364
CONECT   366   367   363
CONECT   367   366   368   369
CONECT   368   367
```

-42-

```
CONECT  369  367
CONECT  370  364  372  371
CONECT  371  370
CONECT  372  370  373  375
CONECT  373  374  372  381
CONECT  374  373
CONECT  375  376  372
CONECT  376  375  377  378
CONECT  377  376
CONECT  378  376  379  380
CONECT  379  378
CONECT  380  378
CONECT  381  373  383  382
CONECT  382  381
CONECT  383  381  384  386
CONECT  384  385  383  391
CONECT  385  384
CONECT  386  387  383
CONECT  387  386  388
CONECT  388  387  389  390
CONECT  389  388
CONECT  390  388
CONECT  391  384  393  392
CONECT  392  391
CONECT  393  396  391  394
CONECT  394  395  393  399
CONECT  395  394
CONECT  396  393  397  398
CONECT  397  396
CONECT  398  396
CONECT  399  394  401  400
CONECT  400  399
CONECT  401  399  402  404
CONECT  402  403  401  412
CONECT  403  402
CONECT  404  405  401
CONECT  405  404  406
CONECT  406  405  407
CONECT  407  406  408
CONECT  408  407  409  410  411
CONECT  409  408
CONECT  410  408
CONECT  411  408
CONECT  412  402  414  413
CONECT  413  412
CONECT  414  412  415  417
CONECT  415  416  414  429
CONECT  416  415
CONECT  417  418  414
CONECT  418  417  419
CONECT  419  418  420
CONECT  420  419  422  421
CONECT  421  420
CONECT  422  420  423  426
CONECT  423  422  424  425
CONECT  424  423
CONECT  425  423
CONECT  426  422  427  428
CONECT  427  426
CONECT  428  426
```

```
CONECT   429   415   431   430
CONECT   430   429
CONECT   431   434   429   432
CONECT   432   433   431   435
CONECT   433   432
CONECT   434   431
CONECT   435   432   437   436
CONECT   436   435
CONECT   437   435   438   440
CONECT   438   439   437   447
CONECT   439   438
CONECT   440   441   437
CONECT   441   440   442
CONECT   442   441   443   444
CONECT   443   442
CONECT   444   442   445   446
CONECT   445   444
CONECT   446   444
CONECT   447   438   449   448
CONECT   448   447
CONECT   449   447   450   452
CONECT   450   451   449   464
CONECT   451   450
CONECT   452   453   449
CONECT   453   452   454
CONECT   454   453   455
CONECT   455   454   457   456
CONECT   456   455
CONECT   457   455   458   461
CONECT   458   457   459   460
CONECT   459   458
CONECT   460   458
CONECT   461   457   462   463
CONECT   462   461
CONECT   463   461
CONECT   464   450   466   465
CONECT   465   464
CONECT   466   469   464   467
CONECT   467   468   466   476
CONECT   468   467
CONECT   469   466   470
CONECT   470   469   471
CONECT   471   470   472   473
CONECT   472   471
CONECT   473   471   475   474
CONECT   474   473
CONECT   475   473
CONECT   476   467   478   477
CONECT   477   476
CONECT   478   476   479   481
CONECT   479   480   478   484
CONECT   480   479
CONECT   481   482   483   478
CONECT   482   481
CONECT   483   481
CONECT   484   479   486   485
CONECT   485   484
CONECT   486   489   484   487
CONECT   487   488   486   492
CONECT   488   487
```

```
CONECT  489  486  490  491
CONECT  490  489
CONECT  491  489
CONECT  492  487  494  493
CONECT  493  492
CONECT  494  492  495  497
CONECT  495  496  494  498
CONECT  496  495
CONECT  497  494
CONECT  498  495  500  499
CONECT  499  498
CONECT  500  498  501
CONECT  501  502  500  503
CONECT  502  501
CONECT  503  501  505  504
CONECT  504  503
CONECT  505  503  506  508
CONECT  506  507  505  512
CONECT  507  506
CONECT  508  509  505
CONECT  509  508  510  511
CONECT  510  509
CONECT  511  509
CONECT  512  506  514  513
CONECT  513  512
CONECT  514  512  515  517
CONECT  515  516  514  523
CONECT  516  515
CONECT  517  518  514
CONECT  518  517  519  520
CONECT  519  518
CONECT  520  518  521  522
CONECT  521  520
CONECT  522  520
CONECT  523  515  525  524
CONECT  524  523
CONECT  525  523  526  528
CONECT  526  527  525  535
CONECT  527  526
CONECT  528  529  525
CONECT  529  528  530  531
CONECT  530  529  532
CONECT  531  529  533
CONECT  532  530  534
CONECT  533  531  534
CONECT  534  532  533
CONECT  535  526  537  536
CONECT  536  535
CONECT  537  535  538  540
CONECT  538  539  537  552
CONECT  539  538
CONECT  540  541  537
CONECT  541  540  542
CONECT  542  541  543
CONECT  543  542  545  544
CONECT  544  543
CONECT  545  543  546  549
CONECT  546  545  547  548
CONECT  547  546
CONECT  548  546
```

```
CONECT  549  545  550  551
CONECT  550  549
CONECT  551  549
CONECT  552  538  554  553
CONECT  553  552
CONECT  554  552  555  557
CONECT  555  556  554  561
CONECT  556  555
CONECT  557  558  559  554
CONECT  558  557  560
CONECT  559  557
CONECT  560  558
CONECT  561  555  563  562
CONECT  562  561
CONECT  563  561  564  566
CONECT  564  565  563  570
CONECT  565  564
CONECT  566  567  569  563
CONECT  567  566  568
CONECT  568  567
CONECT  569  566
CONECT  570  564  572  571
CONECT  571  570
CONECT  572  570  573  575
CONECT  573  574  572  584
CONECT  574  573
CONECT  575  576  572
CONECT  576  575  577  578
CONECT  577  576  579
CONECT  578  576  580
CONECT  579  577  581
CONECT  580  578  581
CONECT  581  579  580  582
CONECT  582  581  583
CONECT  583  582
CONECT  584  573  586  585
CONECT  585  584
CONECT  586  584  587  589
CONECT  587  588  586  592
CONECT  588  587
CONECT  589  590  586
CONECT  590  589  591
CONECT  591  590
CONECT  592  587  594  593
CONECT  593  592
CONECT  594  592  595  597
CONECT  595  596  594  601
CONECT  596  595
CONECT  597  598  599  594
CONECT  598  597  600
CONECT  599  597
CONECT  600  598
CONECT  601  595  603  602
CONECT  602  601
CONECT  603  601  604  606
CONECT  604  605  603  609
CONECT  605  604
CONECT  606  607  608  603
CONECT  607  606
CONECT  608  606
```

```
CONECT  609  604  611  610
CONECT  610  609
CONECT  611  609  612  614
CONECT  612  613  611  621
CONECT  613  612
CONECT  614  615  611
CONECT  615  614  616
CONECT  616  615  617  618
CONECT  617  616
CONECT  618  616  619  620
CONECT  619  618
CONECT  620  618
CONECT  621  612  623  622
CONECT  622  621
CONECT  623  626  621  624
CONECT  624  625  623  630
CONECT  625  624
CONECT  626  623  627  629
CONECT  627  626  628
CONECT  628  627
CONECT  629  626
CONECT  630  624  632  631
CONECT  631  630
CONECT  632  630  633  635
CONECT  633  634  632  641
CONECT  634  633
CONECT  635  636  632
CONECT  636  635  637  638
CONECT  637  636
CONECT  638  636  639  640
CONECT  639  638
CONECT  640  638
CONECT  641  633  643  642
CONECT  642  641
CONECT  643  646  641  644
CONECT  644  645  643  648
CONECT  645  644
CONECT  646  643  647
CONECT  647  646  762
CONECT  648  649  644
CONECT  649  648  650  652
CONECT  650  651  649  655
CONECT  651  650
CONECT  652  653  649
CONECT  653  652  654
CONECT  654  653
CONECT  655  650  657  656
CONECT  656  655
CONECT  657  660  655  658
CONECT  658  659  657  668
CONECT  659  658
CONECT  660  657  661
CONECT  661  660  662
CONECT  662  661  663
CONECT  663  662  664
CONECT  664  663  667  666  665
CONECT  665  664
CONECT  666  664
CONECT  667  664
CONECT  668  658  670  669
```

```
CONECT   669   668
CONECT   670   668   671   673
CONECT   671   672   670   678
CONECT   672   671
CONECT   673   674   670
CONECT   674   673   675
CONECT   675   674   676   677
CONECT   676   675
CONECT   677   675
CONECT   678   671   680   679
CONECT   679   678
CONECT   680   678   681   683
CONECT   681   682   680   689
CONECT   682   681
CONECT   683   684   680
CONECT   684   683   685   686
CONECT   685   684
CONECT   686   684   687   688
CONECT   687   686
CONECT   688   686
CONECT   689   681   691   690
CONECT   690   689
CONECT   691   689   692   694
CONECT   692   693   691   701
CONECT   693   692
CONECT   694   695   691
CONECT   695   694   696   697
CONECT   696   695   698
CONECT   697   695   699
CONECT   698   696   700
CONECT   699   697   700
CONECT   700   698   699
CONECT   701   692   703   702
CONECT   702   701
CONECT   703   701   704   706
CONECT   704   705   703   710
CONECT   705   704
CONECT   706   707   703
CONECT   707   708   708   709
CONECT   708   707
CONECT   709   707
CONECT   710   712   704   711
CONECT   711   710
CONECT   712   710   713   715
CONECT   713   714   712   722
CONECT   714   713
CONECT   715   716   712
CONECT   716   715   717   718
CONECT   717   716   719
CONECT   718   716   720
CONECT   719   717   721
CONECT   720   718   721
CONECT   721   719   720
CONECT   722   713   724   723
CONECT   723   722
CONECT   724   722   725   727
CONECT   725   726   724   731
CONECT   726   725
CONECT   727   728   724
CONECT   728   727   729   730
```

```
CONECT  729  728
CONECT  730  728
CONECT  731  725  733  732
CONECT  732  731
CONECT  733  731  734  736
CONECT  734  735  733  740
CONECT  735  734
CONECT  736  737  739  733
CONECT  737  736  738
CONECT  738  737
CONECT  739  736
CONECT  740  734  741  746
CONECT  741  740  742  744
CONECT  742  743  741  747
CONECT  743  742
CONECT  744  745  741
CONECT  745  744  746
CONECT  746  745  740
CONECT  747  742  749  748
CONECT  748  747
CONECT  749  747  750  752
CONECT  750  751  749  756
CONECT  751  750
CONECT  752  753  749
CONECT  753  752  754  755
CONECT  754  753
CONECT  755  753
CONECT  756  750  758  757
CONECT  757  756
CONECT  758  756  759  761
CONECT  759  760  758  763
CONECT  760  759
CONECT  761  762  758
CONECT  762  761  647
CONECT  763  759  765  764
CONECT  764  763
CONECT  765  763  766  768
CONECT  766  767  765  776
CONECT  767  766
CONECT  768  769  765
CONECT  769  768  770
CONECT  770  769  771
CONECT  771  770  772
CONECT  772  771  773  774  775
CONECT  773  772
CONECT  774  772
CONECT  775  772
CONECT  776  766  778  777
CONECT  777  776
CONECT  778  776  779  781
CONECT  779  780  778  784
CONECT  780  779
CONECT  781  782  778
CONECT  782  781  783
CONECT  783  782
CONECT  784  785  779
CONECT  785  784  786  788
CONECT  786  787  785  792
CONECT  787  786
CONECT  788  789  785
```

```
CONECT   789   788   790   791
CONECT   790   789
CONECT   791   789
CONECT   792   786   794   793
CONECT   793   792
CONECT   794   792   795   797
CONECT   795   796   794   808
CONECT   796   795
CONECT   797   798   794
CONECT   798   797   799   800
CONECT   799   798   801
CONECT   800   798   803   804
CONECT   801   799   803   802
CONECT   802   801
CONECT   803   800   801   805
CONECT   804   800   806
CONECT   805   803   807
CONECT   806   804   807
CONECT   807   805   806
CONECT   808   795   810   809
CONECT   809   808
CONECT   810   808   811   813
CONECT   811   812   810   819
CONECT   812   811
CONECT   813   814   810
CONECT   814   813   815   816
CONECT   815   814
CONECT   816   814   817   818
CONECT   817   816
CONECT   818   816
CONECT   819   811   821   820
CONECT   820   819
CONECT   821   819   822
CONECT   822   823   821   824
CONECT   823   822
CONECT   824   822   826   825
CONECT   825   824
CONECT   826   824   827   829
CONECT   827   828   826   833
CONECT   828   827
CONECT   829   830   826
CONECT   830   829   831   832
CONECT   831   830
CONECT   832   830
CONECT   833   827   835   834
CONECT   834   833
CONECT   835   833   836   838
CONECT   836   837   835   842
CONECT   837   836
CONECT   838   839   841   835
CONECT   839   838   840
CONECT   840   839
CONECT   841   838
CONECT   842   836   844   843
CONECT   843   842
CONECT   844   842   845
CONECT   845   846   844   847
CONECT   846   845
CONECT   847   845   849   848
CONECT   848   847
```

```
CONECT  849  847  850  852
CONECT  850  851  849  857
CONECT  851  850
CONECT  852  853  849
CONECT  853  852  854
CONECT  854  853  855  856
CONECT  855  854
CONECT  856  854
CONECT  857  850  859  858
CONECT  858  857
CONECT  859  862  857  860
CONECT  860  861  859  864
CONECT  861  860
CONECT  862  859  863
CONECT  863  862  1049
CONECT  864  860  866  865
CONECT  865  864
CONECT  866  864  867  869
CONECT  867  868  866  873
CONECT  868  867
CONECT  869  870  872  866
CONECT  870  869  871
CONECT  871  870
CONECT  872  869
CONECT  873  867  875  874
CONECT  874  873
CONECT  875  873  876  878
CONECT  876  877  875  882
CONECT  877  876
CONECT  878  879  875
CONECT  879  878  880  881
CONECT  880  879
CONECT  881  879
CONECT  882  876  884  883
CONECT  883  882
CONECT  884  882  885  887
CONECT  885  886  884  893
CONECT  886  885
CONECT  887  888  884
CONECT  888  887  889  890
CONECT  889  888
CONECT  890  888  891  892
CONECT  891  890
CONECT  892  890
CONECT  893  885  895  894
CONECT  894  893
CONECT  895  893  896  898
CONECT  896  897  895  899
CONECT  897  896
CONECT  898  895
CONECT  899  896  901  900
CONECT  900  899
CONECT  901  904  899  902
CONECT  902  903  901  913
CONECT  903  902
CONECT  904  901  905
CONECT  905  904  906  907
CONECT  906  905  908
CONECT  907  905  909
CONECT  908  906  910
```

```
CONECT  909  907  910
CONECT  910  908  909  911
CONECT  911  910  912
CONECT  912  911
CONECT  913  902  915  914
CONECT  914  913
CONECT  915  913  916  918
CONECT  916  917  915  922
CONECT  917  916
CONECT  918  919  920  915
CONECT  919  918  921
CONECT  920  918
CONECT  921  919
CONECT  922  916  924  923
CONECT  923  922
CONECT  924  922  925  927
CONECT  925  926  924  931
CONECT  926  925
CONECT  927  928  924
CONECT  928  927  929  930
CONECT  929  928
CONECT  930  928
CONECT  931  932  925
CONECT  932  931  933  935
CONECT  933  934  932  939
CONECT  934  933
CONECT  935  936  937  932
CONECT  936  935  938
CONECT  937  935
CONECT  938  936
CONECT  939  933  941  940
CONECT  940  939
CONECT  941  939  942  944
CONECT  942  943  941  951
CONECT  943  942
CONECT  944  945  941
CONECT  945  944  946
CONECT  946  945  947  948
CONECT  947  946
CONECT  948  946  949  950
CONECT  949  948
CONECT  950  948
CONECT  951  942  953  952
CONECT  952  951
CONECT  953  951  954  956
CONECT  954  955  953  960
CONECT  955  954
CONECT  956  957  953
CONECT  957  956  958  959
CONECT  958  957
CONECT  959  957
CONECT  960  954  962  961
CONECT  961  960
CONECT  962  960  963  965
CONECT  963  964  962  977
CONECT  964  963
CONECT  965  966  962
CONECT  966  965  967
CONECT  967  966  968
CONECT  968  967  970  969
```

```
CONECT   969   968
CONECT   970   968   971   974
CONECT   971   970   972   973
CONECT   972   971
CONECT   973   971
CONECT   974   970   975   976
CONECT   975   974
CONECT   976   974
CONECT   977   963   979   978
CONECT   978   977
CONECT   979   977   980   982
CONECT   980   981   979   986
CONECT   981   980
CONECT   982   983   984   979
CONECT   983   982   985
CONECT   984   982
CONECT   985   983
CONECT   986   980   988   987
CONECT   987   986
CONECT   988   986   989   991
CONECT   989   990   988   992
CONECT   990   989
CONECT   991   988
CONECT   992   989   994   993
CONECT   993   992
CONECT   994   992   995   997
CONECT   995   996   994   1000
CONECT   996   995
CONECT   997   998   994
CONECT   998   997   999
CONECT   999   998
CONECT   1000  995   1002  1001
CONECT   1001  1000
CONECT   1002  1000  1003  1005
CONECT   1003  1004  1002  1012
CONECT   1004  1003
CONECT   1005  1006  1002
CONECT   1006  1005  1007  1008
CONECT   1007  1006  1009
CONECT   1008  1006  1010
CONECT   1009  1007  1011
CONECT   1010  1008  1011
CONECT   1011  1009  1010
CONECT   1012  1003  1014  1013
CONECT   1013  1012
CONECT   1014  1012  1015  1017
CONECT   1015  1016  1014  1020
CONECT   1016  1015
CONECT   1017  1018  1014
CONECT   1018  1017  1019
CONECT   1019  1018
CONECT   1020  1015  1022  1021
CONECT   1021  1020
CONECT   1022  1020  1023  1025
CONECT   1023  1024  1022  1032
CONECT   1024  1023
CONECT   1025  1026  1022
CONECT   1026  1025  1027
CONECT   1027  1026  1028  1029
CONECT   1028  1027
```

```
CONECT 1029 1027 1030 1031
CONECT 1030 1029
CONECT 1031 1029
CONECT 1032 1023 1034 1033
CONECT 1033 1032
CONECT 1034 1032 1035 1037
CONECT 1035 1036 1034 1043
CONECT 1036 1035
CONECT 1037 1038 1034
CONECT 1038 1037 1039 1040
CONECT 1039 1038
CONECT 1040 1038 1041 1042
CONECT 1041 1040
CONECT 1042 1040
CONECT 1043 1035 1045 1044
CONECT 1044 1043
CONECT 1045 1043 1046 1048
CONECT 1046 1047 1045 1050
CONECT 1047 1046
CONECT 1048 1049 1045
CONECT 1049 1048  863
CONECT 1050 1046 1052 1051
CONECT 1051 1050
CONECT 1052 1050 1053 1055
CONECT 1053 1054 1052 1059
CONECT 1054 1053
CONECT 1055 1056 1052
CONECT 1056 1055 1057 1058
CONECT 1057 1056
CONECT 1058 1056
CONECT 1059 1053 1061 1060
CONECT 1060 1059
CONECT 1061 1059 1062 1064
CONECT 1062 1063 1068 1061
CONECT 1063 1062
CONECT 1064 1065 1066 1061
CONECT 1065 1064 1067
CONECT 1066 1064
CONECT 1067 1065
CONECT 1068 1062
END
```

We claim:

1. A synthetic peptide consisting essentially of an amino acid sequence from about 5 to about 50 amino acids in length, which sequence has a greater than 50% sequence identity with a segment of the portion of the native amino acid sequence of the human kininogen heavy chain comprisinq amino acids 124–232 of the mature kininogen heavy chain, said peptide having an artificially introduced restricted conformation and the ability to inhibit the enzymatic activity of calpain, or a pharmaceutically acceptable salt of said peptide, wherein said peptide, or the salt of said peptide, is optionally attached to an additional linker sequence from about 1 to 100 amino acids in length, which may be further linked to a detectable label, solid matrix, or carrier, and wherein the restricted conformation may be determined from the equilibrium conformation model comprising the set of coordinates and connect statement of Appendix 1.

2. A synthetic peptide consisting essentially of an amino acid sequence from about 5 to about 50 amino acids in length, which sequence has a greater than 50% sequence identity with a segment of the portion of the native amino acid sequence of the human kininogen heavy chain comprtsinq amino acids 124–232 of the mature kininogen heavy chain, said peptide having an artificially introduced restricted conformation and the ability to inhibit the enzymatic activity of calpain wherein said restricted conformation is by means of a cysteine-cysteine disulfide bond wherein at least one of the cysteine residues which form the disulfide bond is not present in the native amino acid sequence of the mature kininogen heavy chain, or a pharmaceutically acceptable salt of said peptide, wherein said peptide is optionally attached to an additional linker sequence from about 1 to 100 amino acids in length, which may be further attached to a detectable label, solid matrix, or carrier, and wherein the restricted conformation may be determined from the equilibrium conformation model comprising the set of coordinates and connect statement of Appendix 1.

3. A peptide according to claim 2 wherein the peptide is between 6 and about 20 amino acids in length.

4. A peptide according to claim 2 wherein the peptide comprises amino acids 211–230 of the kininogen heavy chain.

5. A synthetic peptide consisting essentially of an amino acid sequence from about 5 to about 50 amino acids in length, which sequence has a greater than 50% sequence identity with a segment of the portion of the native amino acid sequence of the human kininogen heavy chain comprising amino acids 124–232 of the mature kininogen heavy chain, said peptide having an artificially introduced restricted conformation and the ability to inhibit the enzymatic activity of calpain, wherein said restricted conformation is by means of an artificially introduced covalent bond, or a pharmaceutically acceptable salt of said peptide, wherein said peptide or salt of said peptide is optionally attached to an additional linker sequence from about 1 to 100 amino acids in length, which may be further attached to a detectabie label, solid matrix, or carrier, and wherein the restricted conformation may be determined from the quilibrium conformation model comprising the set of coordinates and connect statement of Appendix 1.

6. A peptide according to claim 5 wherein the restricted conformation is restricted by means of an amide bond formed between side chains of a lysine residue and a glutamic or an aspattic acid residue.

7. A peptide according to claim 5 wherein the restricted conformation is restricted by means of a toluene-2-4-diisocyanate cross-linked between two free amino groups of said peptide.

8. A pharmaceutical composition comprising a peptide of claim 1 and a pharmaceutically acceptable carrier.

9. A pharmaceutical composition comprising a peptide of claim 2 and a pharmaceutically acceptable carrier.

10. A pharmaceutical composition comprising a peptide of claim 4 and a pharmaceutically acceptable carrier.

11. A peptide accordinq to claim 1, wherein said linker sequence is affixed to a detectable label, solid matrix or carrier.

12. A peptide according to claim 1 which is from about 6 to about 26 amino acids in length.

13. A peptide according to claim 1 wherein the peptide comprises amino acids 211–230 of the kininogen heavy chain.

14. A pharmaceutical composition comprising a peptide of claim 1 and a pharmaceutically acceptable carrier.

15. A peptide according to claim 5, wherein the peptide is between 6 and about 20 amino acids in length.

16. A peptide according to claim 5, wherein the peptide comprises amino acids 211–230 of the kininogen heavy chain.

17. A peptide according to claim 5, wherein the restriction is by means of an amide bond.

18. A peptide according to claim 17, wherein said amide bond is formed between side chains of a lysine residue and a glutamic or an aspattic acid residue.

19. A peptide according claim 5, wherein the restricted conformation is restricted by means of a toluene-2-4-diisocyanate cross-linked between two free amino groups of said peptide.

20. A pharmaceutical composition comprising a peptide according to claim 5 and a pharmaceutically acceptable carrier.

21. A synthetic peptide according to claim 1 which has a greater than 90% sequence identity with said segment of the kininogen heavy chain native amino acid sequence.

22. A synthetic peptide according to claim 2 which has a greater than 90% sequence identity with said segment of the kininogen heavy chain native amino acid sequence.

23. A synthetic peptide according to claim 5 which has a greater than 90% sequence identity with said segment of the kininogen heavy chain native amino acid sequence.

24. A synthetic peptide according to claim 1 wherein zero, one or two amino acids are substituted, deleted or inserted with respect to the native amino acid sequence of said segment of the kininogen heavy chain native amino acid sequence.

25. A synthetic peptide according to claim 2 wherein the amino acid sequence of the peptide differs from said seqment of the kininogen heavy chain native amino acid sequence in the substitution of one or more non-cysteine amino acids with cysteine amino acids, or the insertion of one or more cysteine amino acids into the native sequence.

26. A sythetic peptide according to claim 25 wherein two non-cystein amino acids are substituted with cysteine amino acids, or two cysteine amino acids are inserted into the native sequence.

27. A synthetic peptide according to claim 5 wherein one or two amino acids are substituted, deleted or inserted with respect to the native amino acid sequence of said seqment of the kininogen heavy chain native amino acid sequence.

28. A peptide according to claim 13 wherein the peptide is SEQ ID NO:1.

29. A pharmaceutical composition comprising the according to claim 28 and a pharmaceutically acceptable carrier.

30. A peptide analog of human kininogen heavy chain consisting essentially of an amino acid sequence which has a greater than 50% sequence identity with SEQ ID NO:1 or a greater than 50% sequence identity with an at least five amino acid fragment of SEQ ID NO:1, said peptide having a restricted conformation and the ability to inhibit the enzyme activity of calpain.

31. A peptide according to claim 28 which has a greater than 90% sequence identity with SEQ ID NO:1, or a greater than 90% sequence identity with an at least five amino acid fragment of SEQ ID NO:1.

32. A peptide consisting essentially of an amino acid sequence identical to SEQ ID NO:1 or identical to an at least five amino acid fragment of SEQ ID NO:1, but for the substitution or insertion of one or two amino acids, said peptide having a restricted conformation and the ability to inhibit the enzyme activity of calpain.

33. A pharmaceutical composition comprising a peptide of claim 13 and a pharmaceutically acceptable carrier.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 amino acids
( B ) TYPE: amino acid
( C ) TOPOLOGY: linear ( x i ) SEQUENCE DESCRIPTION: SEQ ID NO:1:

```
Cys  Thr  Asp  Asn  Ala  Tyr  Ile  Asp  Ile  Gln
                         5                      10
Leu  Arg  Ile  Ala  Ser  Phe  Ser  Gln  Asn  Cys
                        15                      20
```

( 2 ) INFORMATION FOR SEQ ID NO:2:

( i ) SEQUENCE CHARACTERISTICS:
( A ) LENGTH: 5 amino acids
( B ) TYPE: amino acid
( C ) TOPOLOGY: linear ( x i ) SEQUENCE DESCRIPTION: SEQ ID NO:2:

```
Gln  Val  Val  Ala  Gly
                     5
```